United States Patent
Derda et al.

(10) Patent No.: US 10,900,061 B2
(45) Date of Patent: Jan. 26, 2021

(54) METHOD FOR DETECTING A SUBSTANCE IN A SAMPLE USING MODIFIED BACTERIOPHAGES

(71) Applicant: The Governors of the University of Alberta, Edmonton (CA)

(72) Inventors: Ratmir Derda, Edmonton (CA); Maribel Elizabeth Funes Huacca, Sao Paulo (BR); Simon Ng, Edmonton (CA); Katrina Felicia Tjhung, Calgary (CA)

( * ) Notice: Subject to any disclaimer, the term of this patent is extended or adjusted under 35 U.S.C. 154(b) by 0 days.

(21) Appl. No.: 15/456,177

(22) Filed: Mar. 10, 2017

(65) Prior Publication Data

US 2017/0253904 A1    Sep. 7, 2017

Related U.S. Application Data

(62) Division of application No. 14/354,539, filed as application No. PCT/CA2012/050771 on Oct. 29, 2012, now Pat. No. 9,624,523.

(60) Provisional application No. 61/552,160, filed on Oct. 27, 2011.

(51) Int. Cl.
| | |
|---|---|
| *C12Q 1/18* | (2006.01) |
| *C12M 1/04* | (2006.01) |
| *C12M 1/00* | (2006.01) |
| *C12M 3/00* | (2006.01) |
| *C12M 1/12* | (2006.01) |
| *C12Q 1/02* | (2006.01) |

(52) U.S. Cl.
CPC .............. *C12Q 1/18* (2013.01); *C12M 23/24* (2013.01); *C12M 23/34* (2013.01); *C12M 23/54* (2013.01); *C12M 25/02* (2013.01); *C12M 29/04* (2013.01); *C12Q 1/02* (2013.01); *C12N 2795/00011* (2013.01); *C12N 2795/00031* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| 6,043,079 A | 3/2000 | Leighton |
| 2011/0105360 A1 | 5/2011 | Derda et al. |

FOREIGN PATENT DOCUMENTS

| EP | 0279077 A2 | 8/1988 |
| EP | 1 266 963 A1 | 12/2002 |
| GB | 2 428 293 A | 1/2007 |
| WO | WO 1999/058655 A2 | 11/1999 |
| WO | WO 2007/010525 A2 | 1/2007 |
| WO | WO2009/108229 A2 | 9/2009 |
| WO | WO 2009/120963 | 10/2009 |

OTHER PUBLICATIONS

Cebe and Geiser, Biochem. J., 2000, 352:841-849. (Year: 2000).*
International Search Report with Written Opinion corresponding to International Patent Application No. PCT/CA2012/050771, dated Jan. 30, 2013.
Derda et al. (2009) "Paper-supported 3D cell culture for tissue based bioassays,"Proc. Natl. A cad. Sci. U. S. A. 1 06:1 845 7-1 8462.
Derda et al. (May 6, 2011) "Multizone Paper Platform for 3D Cell Cultures," PLOS One. 6:1-13.
Funes-Huacca et al. (Aug. 15, 2012) "Portable self-contained culture for phage and bacteria made of paper and tape," Lab Chip. 12:4269-4278.
Ng et al. (Oct. 31, 2011) "Bacteriophages and viruses as a support for organic synthesis and combinatorial chemistry," ACS Chemical Biology. 7:123-138.
International Preliminary Report on Patentability dated Apr. 29, 2014 corresponding to International Patent Application No. PCT/CA2012/050771.
Communication pursuant to Rule 164(1) EPC dated Apr. 8, 2015, for corresponding European Patent Application No. 12844273.8.
Krebber et al., J. Mol. Bioi., 1997,268:607-618.
Supplementary European Search Report with Written Opinion corresponding to European Patent Application No. 12844273, dated Oct. 23, 2015.
Ripp, Adv Biochem Engin/Biotechnol, 2010, 118:65-83; Published online: May 21, 2009.

* cited by examiner

*Primary Examiner* — Nicole Kinsey White
(74) *Attorney, Agent, or Firm* — Bennett Jones LLP

(57) ABSTRACT

The present invention provides a binding assay that employs an activatable dormant bacteriophage carrying a reporter gene to qualitatively or quantitatively detect the presence of a substance of interest in a sample. Also provided is a simple culture device that is designed for manufacture and use in areas of limited resources. The device is useful for cell culture in such environments with limited resources because cells grow in paper just as they do in a culture dish.

6 Claims, 29 Drawing Sheets
Specification includes a Sequence Listing.

METHOD FOR DETECTING A SUBSTANCE IN A SAMPLE USING MODIFIED BACTERIOPHAGES

CROSS-REFERENCE TO RELATED APPLICATIONS

This application is a divisional application of U.S. application Ser. No. 14/354,539, filed Apr. 25, 2014, now U.S. Pat. No. 9,624,523, which is a U.S. National Stage Application filed under 35 U.S.C. § 371 of International Application No. PCT/CA2012/050771, filed Oct. 29, 2012, which claims the benefit of U.S. Provisional Application No. 61/552,160, filed Oct. 27, 2011. Each of these applications is hereby incorporated by reference in its entirety.

FIELD OF THE INVENTION

The present application pertains to the field of diagnostic assays and culture devices. In particular, the present invention relates to a point-of-care device and an assay for measuring substances of interest in any environment, including in areas with limited resources.

BACKGROUND

Many diagnostic tests are designed for use in well-equipped clinical labs. There are fundamental limitations to using and producing these tests in a resource-limited environment, especially those in developing nations where laboratory equipment and diagnostic tools are scarce or non-existent. The requirements for most basic diagnostic tests are i) liquid handling; ii) measurement of liquids and reagents; iii) mixing of liquids and reagents; iv) incubation of reagents; v) a binding assay that senses the presence of the analyte to be detected; vi) amplification of the detection signal; and vii) the readout and analysis of the detected signal. The foregoing requirements are difficult if not impossible to meet in a developing country, especially those areas with limited resources, for example refugee camps. It is precisely in such resource limited environments where a simple, low cost detection device and method are required. Additional requirements for diagnostic tests in developing countries must take into consideration the following: viii) the use of low-cost, on-site components; ix) the ability to produce devices without advanced infrastructure i.e., in the absence of roll-to-roll, robotic, conveyer belt and/or injection molding processes etc.; x) simple storage in the absence of refrigeration and/or incubation of samples; and xi) a lack of electricity to power diagnostic equipment.

Most if not all diagnostic assays satisfying criteria i) to vii) require production in advanced settings. Examples include devices that require high-resolution microfluidic channels, electronic components, and reagents that require storage at low temperature. However, such devices and systems do not satisfy requirements viii) to xi), and are not suitable for production or use in low-resource environments or in the field.

Phage display is a well know technique used in the analysis, display and production of protein antigens, especially human proteins of interest. Phage display is a process during which the phage, a bacterial virus, is made to expose or "display" different peptides or proteins including human antibodies on its surface. Through genetic engineering, peptides or proteins of interest are attached individually to a phage cell surface protein molecule (usually Gene III protein, g3p). In such a phage population (phage library), each phage carries a gene for a different peptide or protein—g3p fusion and exposes it on its surface. Through a variety of selection procedures, phages that "display" binders to specific target molecules of interest can be identified and isolated. The phage display technique is very useful in discovery and development of pharmaceutical and/or diagnostic products. In phage display the entire phage binds and can be eluted from an immobilized target molecule. Since the phage remains infective it can inject its DNA into bacterial cells and is amplified. The main limitation of phage display, however, is the occurrence of non-specific adsorption of phages during the binding stage, which necessitates enrichment over several rounds and individually tailored washing and elution conditions. Detection of such enrichment requires sequencing of the phage genome to detect emergence of the specific binding motif. Accordingly, these requirements make phage display technology impractical for diagnostic detection in low-resource environments.

Selectively infective phage (SIP) technology is another technique which can be used to screen large libraries of proteins or other oligo- or polypeptides to select antibodies having high affinity for a target antigen. This technology is described in U.S. Pat. No. 5,514,548. SIP technology is related to phage display technology in that it uses filamentous phages, where a protein of interest is fused to a phage coat protein and, thus, displayed on the outer surface of the phage, while its genetic information is contained in the phage DNA. In contrast to phage display, the phage particles in SIP technology are rendered non-invective by disconnecting the N-terminal domains (N1 and N2) of the phage g3p coat protein which are involved in docking to and penetrating a bacterial cell from the C-terminal domain (CT), which caps the end of the phage. The N- and C-terminal domains are then each fused to one of the interacting partners being studied. One partner is displayed on the phage surface associated with the CT, while the other is genetically fused or chemically coupled to the NT(s), thus making a separate adapter molecule. Only when the specific protein-ligand interaction occurs between the partners is the g3p reconstituted so that the phage particle regains its infectivity, and the genetic information of a successful binder is propagated. The main advantages of SIP technology over phage display are i) that it can be carried out in a continuous manner, which mimics the in vivo system of clonal selection used by the immune system for antibody optimization; ii) no solid-phase interaction with a support is required, reducing the occurrence of non-specific interactions and eliminating the need for elution; iii) reduction of background infectivity; and iv) high sensitivity as single binding events are detectable. However, for SIP technology to achieve these advantages, the genome of SIP must be non-infective rendering the progeny of SIP also non-infective. Amplification of signal in SIP, therefore is limited. SIP also necessitates genetic fusion or chemical covalent attachment of the binding partners to the coat proteins of phage. Binding of molecules that are not covalently attached to phage proteins cannot be detected by SIP technology. Extension of SIP to detection of soluble analytes, as it is necessary for diagnostic applications, is not obvious. These limitations make SIP technology unsuitable as a diagnostic technique.

Three-dimensional cellular arrays have been well described in WO 2009/120963 (Derda et al. (1)) and in "Paper-Supported 3D Cell Culture for Tissue-Based Bioassays" Proc. Natl. Acad. Sci. 2009, 106(44), 18457-18462, (Derda et al. (2)). The three-dimensional cellular arrays include a porous hydrophilic substrate with a number of porous regions bounded at least in part by a liquid impervious boundary and a hydrogel comprising cells, wherein the hydrogel is embedded within the porous regions of the device. The substrate may be constructed from paper, nitrocellulose, cellulose acetate, cloth, or porous polymer film.

These three-dimensional cellular arrays have been used to characterize various properties of cells grown within the arrays using well known cellular assays, including apoptosis, cell proliferation, cell cycle and gene expression. The three-dimensional cellular arrays may also be used to assay any one or more synthetic, naturally occurring, or a combination of synthetic and natural test agent, for example urine, blood, tears, sweat, or saliva, wherein a change in cellular function in the presence of the one or more test agents indicates the one or more test agents modify cellular function. However, in order to mimic a three-dimensional environment most of the cellular arrays disclosed in WO 2009/120963 require a hydrogel or hydrogel precursor be embedded within the porous regions. The viability of *Pseudomonas aeruginosa* strain PA 14 cells grown in a stack of 200 micron chromatography paper was investigated as set out in Example 9 of WO 2009/120963. The result was that a steady decrease in the number of both live and dead bacteria in the middle of the array was observed. This was attributed to competing rates of oxygen diffusion and oxygen consumption by the bacteria. All examples and claim presented in the WO 2009/120963 use paper-based 3D culture as a part of another sterile culture, such as submersions in sterile media incubated in a sterile container, housed inside a humidity and temperature controlled aseptic environment with humidity and temperature control. It is nonobvious how to extend this invention to create an autonomous setup that requires no secondary sterile container and no aseptic incubator. Accordingly, the difficulty in maintaining cell viability within the three-dimensional cellular arrays as well as the need for advanced incubation and imaging equipment to monitor biological activity within these types of 3-D arrays makes them inadequate for the purposes of a simple diagnostic assay.

Given the foregoing, there remains a need for a diagnostic device and method that can be easily constructed from simple components, on-site in low-resource environments.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide a diagnostic device and assay method.

In accordance with one aspect, there is provided a portable culture device comprising: a first culture strip comprising at least one culture region within a first strip of impermeable material having an adhesive on its inner surface; a second culture strip comprising at least one culture region within a second strip of impermeable material having an adhesive on its inner surface, wherein each of the at least one culture regions of the second culture strip corresponds to one of the at least one culture regions of first culture strip to form a culture region pair, wherein each culture region comprises an inner layer of porous hydrophilic material and at least one culture region in each culture region pair comprises an outer layer of a gas permeable membrane, and wherein the device is moveable between an open condition and a closed condition in which the first and second culture strips are releasably adhered via the inner adhesive surfaces such that the culture regions in each culture pair are aligned and the outer gas permeable membrane or gas permeable membranes are exposed to the environment to permit gas flow to the interior of the device.

In accordance with another aspect, there is provided a method for detecting a substance of interest in a sample, comprising the steps of: introducing the sample to a mixture of dormant bacteriophage, bacteria, and a soluble N-terminal fragment of a phage coat protein, wherein the dormant bacteriophage comprises a reporter gene, and a coat protein from which an N-terminal portion has been removed to produce a truncated coat protein that renders the bacteriophage non-infective and wherein the truncated coat protein displays a first binding ligand for the substrate of interest, where the first binding ligand comprises a peptide fused genetically to the truncated coat protein, or a non-peptidic binding moiety introduced through chemical modification of the truncated coat protein; and wherein the soluble N-terminal fragment comprises a second binding ligand for the substrate of interest, where second binding ligand is comprises a peptide fused genetically to the N-terminal fragment, or a non-peptidic binding moiety introduced through chemical modification of the N-terminal fragment; incubating the mixture of the dormant bacteriophage, bacteria and the soluble N-terminal fragment in the presence of the sample, which, in the presence of the substance of interest, leads to the formation of a complex between the dormant bacteriophage, the substance of interest and the soluble N-terminal fragment; wherein formation of the complex activates the dormant bacteriophage to become infective; culturing the activated bacteriophage with the bacteria; and monitoring for expression of the reporter gene as an indicator of the presence of the substance of interest in the sample.

In one embodiment, the method for detecting a substance of interest is performed using a portable culture device as described herein.

In accordance with another aspect, there is provided a kit for performing the above method for detecting a substance of interest comprising a portable culture device as described herein and instructions for use. The kit can additionally include one or more of: (i) a container of bacteria, (ii) a container of dormant bacteriophage that comprises a reporter gene and a coat protein from which an N-terminal portion has been removed to produce a truncated coat protein that renders the bacteriophage non-infective and wherein the truncated coat protein displays a binding ligand on the surface of the dormant bacteriophage that specifically binds to a substance of interest; and (iii) a container of a recognition molecule that specifically binds to the substance of interest and that comprises an N-terminal portion of the coat protein, wherein formation of a binding complex between the dormant bacteriophage, the substance of interest and the recognition molecule activates the dormant bacteriophage to become infective. In certain embodiments, two or more of components (i)-(iii) are included in a single container.

In accordance with another aspect, there is provided a genetically engineered bacteriophage comprising a modified coat protein gene that expresses a chimeric coat protein having a protease cleavage site on the N-terminal side of a polypeptide binding ligand or a chemical modification site, wherein cleavage at the protease cleavage site truncates the chimeric coat protein by removal of an N-terminal peptide and results in display of the polypeptide binding ligand on the surface of the bacteriophage or exposes the chemical modification site for chemical modification of the bacteriophage with a non-peptidic binding ligand.

BRIEF DESCRIPTION OF THE FIGURES

For a better understanding of the present invention, as well as other aspects and further features thereof, reference is made to the following description which is to be used in conjunction with the accompanying drawings, where:

FIG. 1A is an outer surface view of the device and FIG. 1B is a cross-section view of the device through A-A in FIG. 1A;

FIGS. 16A and 16B illustrate intensity of color using Alamar Blue Dye as a function of time. FIGS. 16C and 16E illustrate detection of microorganisms in various samples. FIG. 16D illustrates graphically the detection of microorganisms on culture plates.

FIG. 21A shows a control Agar Petri dish with 2 antibiotic disks; ampicillin and kanamycin (5 µg) and inoculated with $E.\ coli$ O157:H7 $10^6$; and FIG. 21B shows a culture device using patterned paper with 2 reservoirs for ampicillin (5 µg) and kanamycin (5 µg), respectively, and then inoculated with $E.\ coli$ O157:H7 $10^6$ CFU. All devices were incubated at 37° C. for 18 h and then revealed with Presto Blue®;

FIG. 22A shows a control Agar Petri dish with 2 antibiotic disks; ampicillin and kanamycin (5 µg) and inoculated with $S.\ typhimurium$ PWM 1007 $10^6$ CFU; FIG. 22B shows a culture device using patterned paper with 2 reservoirs for ampicillin (5 µg) and kanamycin (5 µg); respectively and then inoculated with $S.\ typhimurium$ PWM 1007 $10^6$ CFU. All devices were incubated at 37° C. for 18 h and then revealed with Presto Blue®;

FIGS. 23A and C show the steps for engineering the phage. FIG. 23B shows validation of cloning by agarose gel; FIG. 23D shows that on digestion of phage by protease up to 99.9999% of phage can be digested; FIG. 23E shows ELISA assay which demonstrates that engineered AATA phage contains FLAG epitope and binds specifically to anti-FLAG-antibody. It does not bind to non-specific protein (BSA). Non-engineered phage does not bind to FLAG antibody. Other epitopes could be introduced and tested similarly;

DETAILED DESCRIPTION

Definitions

Figure 1A:
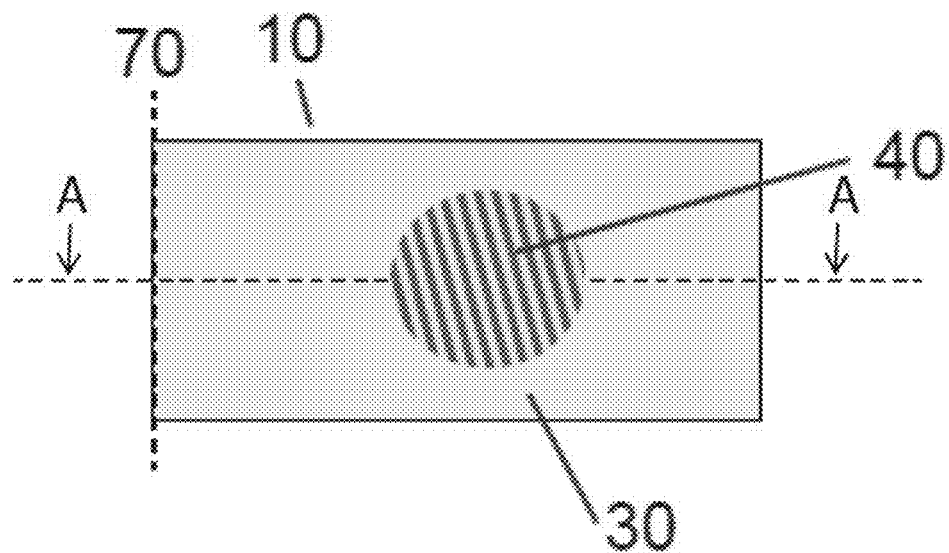
FIGS. 1A and B schematically depict an example of a culture device as described herein, where

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "assay" is used herein to refer to a test to qualitatively or quantitatively detect the presence of a substance in a sample.

The term "biological sample" is used herein to refer to both animal and human body fluids, excreta and tissues obtained from a living or dead organism. The term "body fluid", as used herein includes a naturally occurring and/or secreted and/or excreted and/or discharged fluid and/or wash fluid from the surface or inside the bodies of a human or an animal and includes, but is not limited to: saliva, sputum, serum, plasma, blood, pharyngeal, nasal/nasal pharyngeal and sinus secretions, urine, mucous, feces, chyme, vomit, gastric juices, pancreatic juices, semen/sperm, cerebral spinal fluid, products of lactation or menstruation, egg yolk, amniotic fluid, aqueous humour, vitreous humour, cervical secretions, vaginal fluid/secretions, bone marrow aspirates, pleural fluid, sweat, pus, tears, lymph and bronchial or lung lavage.

The terms "body tissue" or "tissue", as used herein, refer to an aggregate of cells usually of a particular kind together with their intercellular substance that form one of the structural materials of a plant or an animal and that in animals include, for example, connective tissue, epithelium, mucosal membrane, muscle tissue, placental tissue, and tissue from liver, intestines, spleen, kidney, brain, heart, nerve tissue, and the like. Samples of body tissue can be obtained from living humans or animals by a variety of non-limiting methods, such as fine needle aspirates, scrapings or biopsy tissue or from the remains of dead humans or animals. The term "tissue" can be used to refer to naturally occurring tissue or synthetic tissue.

Biological samples can also include pre-processed foodstuffs including plants, samples of meats and processed foods, as well as swab samples from environmental sources such as food processing facilities, hospitals, water, soil, and air. Other biological sample types include isolates/fractions/concentrates of blood (e.g. platelets, red blood cells, white blood cells or leukocytes), including umbilical cord blood or placental blood, bone marrow, aspirates, fine needle organ or lesion aspirates, cervical samples, cultured cells, body swabs, or body smears.

The terms "dormant bacteriophage" and "dormant phage" are used interchangeably to refer to bacteriophage that is non-infective, but that will become infective following activation.

As used herein, the term "reporter gene" refers to a coding sequence attached to heterologous promoter or enhancer elements and whose expression product can be assayed easily and quantifiably when the construct is introduced into bacteria, for example through infection by bacteriophage carrying the reporter gene. Examples include, but not limited to green fluorescent protein and other fluorescent proteins, luciferase and other luminescent proteins, galactosidase and other enzymes activity of which could be detected, antibiotic resistance genes that equip bacteria with antibiotic resistance.

As used herein, the term "binding ligand" refers to an organic molecule that binds to a specific molecule present in a biological sample. The ligands can be polypeptides or "non-peptidic ligands", the latter comprised of polynucleotides, oligosaccharides, and synthetic or natural organic molecules or a combination of all above (for example, a polypeptide chemically modified by oligosaccharide or a polynucleotide chemically modified by an organic molecule). An example of ligand is a "FLAG peptide" or "FLAG epitope" that refers to a polypeptide protein tag that can be added to a protein using recombinant DNA technology. The FLAG peptide, or epitope, is a short, hydrophilic 8-amino acid peptide (Asp-Tyr-Lys-Asp-Asp-Asp-Asp-Lys) (SEQ. ID NO.:1) (A. Einhauer and A. Jungbaeur (2001) "The FLAG™ peptide, a versatile fusion tag for the purification of recombinant proteins." *J. Biochem. Biophys. Methods* 49:455-65). Other polypeptide ligands can be used in the system analogously by trained in the art of molecular biology. An example of non-peptidic ligand is a mannose monosaccharide. Other non-peptidic ligands can be used in the system analogously by anyone trained in the art of bio-conjugation.

The present application provides portable culture devices that facilitate the culture of microorganisms, such as, bacteria (alone, or with bacteriophage) or fungi (e.g., yeast, mold), without the need for complicated or expensive materials and equipment. The culture devices can support the growth of multiple microorganism in a single culture region or in separate culture regions. In certain embodiments the presently described portable culture device can be used to visualize microbial growth. The presence of bacteria, or other microorganisms, can be visualized, for example, by using metabolic dyes or microorganism-specific dyes.

The portable culture devices can be readily adapted for use in assays and methods that include activation of dormant bacteriophage and culture of the activated bacteriophage with bacteria in an assay to indicate the presence of a substance of interest in a biological sample. The present application also provides an assay system for detecting or quantifying a substance in a biological sample. In certain embodiments the presently described portable culture device can be used to visualize reporter genes in the same bacteria. The expression of reporter genes is visualized by a reporter assay, such as fluorescent detection of fluorescent protein, enzymatic detection of the specific enzymes, or detection of antibiotic resistance reporters by promotion or ablation of growth on selective media containing antibiotics. Multiple reporters can be detected simultaneously in the same culture system. For example up to five different fluorescent proteins could be distinguished in this culture and up to four antibiotic reported genes could be tested in one device with 3 cm growth area. A combination of 4×5=20 readouts could be performed in one device.

The culture devices described herein have been designed to be readily produced from simple components that are often on site in resource-limited settings. As such, these diagnostic devices satisfy criteria viii) to xi) described in the Background section above. Further these devices have been designed to permit manufacture and use under a variety of environments and conditions. As will be described in more detail below, the culture device can be manufactured from simple components such as, paper, adhesive tape, gas-permeable membranes, and stocks of engineered bacteria and, optionally, bacteriophage (phage), which can be cultured, processed and stored prior to construction of the device. The device is useable with basic equipment, such as, power-free centrifuges and ovens including ovens.

Culture Device

Figure 1B:
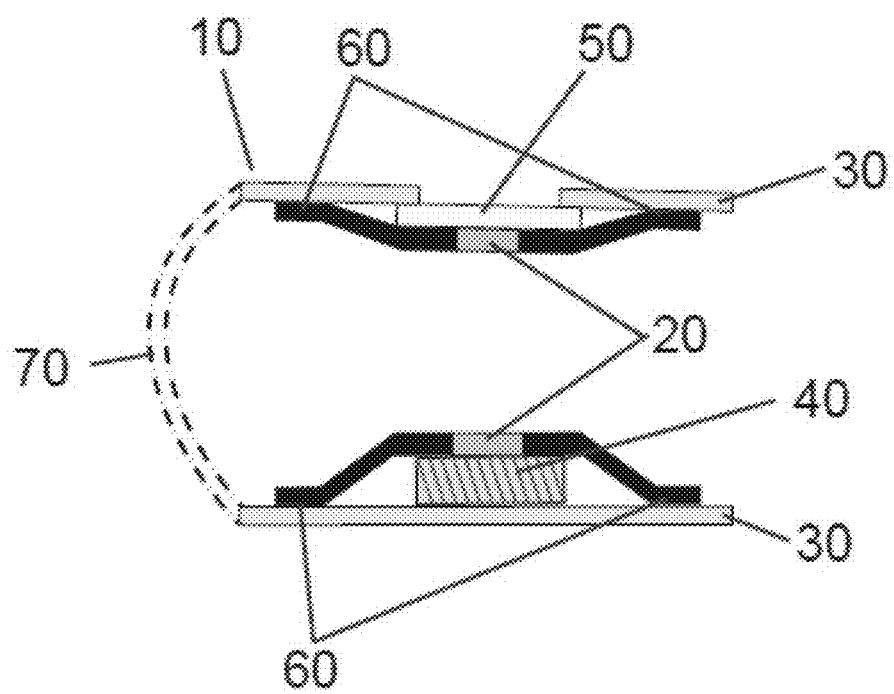

Provided herein is a portable culture device that includes two culture strips. With reference to FIGS. 1A and 1B, each culture strip 10 includes at least one culture region 20 within a strip of fluid (i.e., liquid or gas) impermeable material 30 having an adhesive on its inner surface. The fluid impermeable material can conveniently be, for example, adhesive tape, although any impermeable material that has a single adhesive surface or to which an adhesive layer can be applied, can be used in place of the adhesive tape. Each culture region 20 is made of a porous hydrophilic material that is suitable for supporting culture of bacteria and bacteriophage. One strip contains an inner layer (comprising an adsorbent pad) 40 suitable for wicking and maintaining sufficient amount of liquid for the duration of the culture period. Each culture region in the first culture strip is positioned so that when the culture two strips are brought together (i.e., when closing or sealing the device by folding along the foldable connection region 70) each culture region aligned with a corresponding culture region on the second strip to form a pair. When the device is closed, there is fluid communication between the respective layers of porous hydrophilic material in each culture pair.

For use in culturing microorganisms, such as bacteria and bacteriophage, the porous hydrophilic material in the culture regions is impregnated with culture medium. Selection of the appropriate culture medium is dependent on the microorganism, or combination of microorganisms, to be cultured. Such culture media are now very well known in the field of microbiology such that selection of the appropriate medium is well within the abilities of a skilled worker.

In certain embodiments, the culture device can be used to detect antibiotic resistance or detect presence of resistance genes introduced into bacteria as a result of infection by bacteriophage. In these embodiments, all or a portion of the porous hydrophilic material in the individual culture region (s) is coated or impregnated with an antibiotic of interest. Optionally, all or a portion of the porous hydrophilic material in the individual culture region(s) is patterned with more than one antibiotic of interest. Diffusion of the antibiotic, or antibiotics, within the culture region(s) lead to formation of growth and no-growth zones (for microorganisms sensitive to the antibiotic(s) present). Culture devices having culture regions with a surface area of approximately 3 cm or more can be used to test for resistance to a plurality of antibiotics simultaneously (such as four or more antibiotics). A larger number of antibiotics can be used to pattern culture regions in larger devices.

At least one culture region in each culture pair, includes an outer layer of a gas permeable membrane 50 to permit the flow of gas (e.g., air, oxygen) into the device when it is in a closed condition. Many gas permeable membranes are currently known and are suitable for use in the present culture device. In a specific embodiment, the gas permeable membrane is polydimethylsiloxane ("PDMS"). Selection of the gas permeable membrane can depend on, for example, available resources, and is within the abilities of a worker skilled in the art.

As shown in FIG. 1A, adsorbent pad in the inner layer 40 of porous hydrophilic material is attached at directly to the strip of impermeable material 30 to align with the hole or opening in material 30 when folded along the foldable connection region 70. The porous hydrophilic material 20 has an impermeable circumferential ring 60 of another material, such as wax, that can adhere to the impermeable material of the culture strip to form a water tight seal.

The culture device is moveable between an open condition and a closed condition in which the first and second culture strips are releasably adhered via the inner adhesive surfaces such that the culture regions in each culture pair are aligned and the outer gas permeable membrane or gas permeable membranes are exposed to the environment to permit gas flow to the interior of the device. The closed condition can be used for storage and transport of the device prior to use. Also, the device is in the closed condition during use.

The porous hydrophilic material is a material that can wick liquids and retain the liquid to allow bacterial culture on the material and within its pores. In one embodiment the material is paper. Other readily available soft, porous, hydrophilic materials such as fabric or porous plant components, for example, cotton wool or porous wood can also be used in the culture device. The porous hydrophilic material can be cut into specific shapes and sizes in order to create a reservoir(s) that will adsorb a specific amount of liquid when brought in contact with excess liquid. Measurement of liquids, for example a first liquid containing the bacteriophage and analyte of interest and a second liquid containing the bacteria to be infected, can be achieved with microliter precision by cutting the material in defined mm-size configurations. Liquid handling capacity and reproducibility of using this approach is described in more detail below.

Maintaining two or more sheets of porous hydrophilic material together in between layers of adhesive tape has been found to maintain proper humidity inside each device for the duration of a culture assay, which can range from several hours up to several days.

If a culture assay hinges on growth of the microorganism (viruses, phage, eukaryotic or prokaryotic cells) during the incubation period, the devices must able to maintain proper humidity and permit flow of oxygen as shown in FIGS. 2 to 4. This is achieved through the use of gas permeable films to create devices that allow diffusion of oxygen but maintain humidity inside the culture zone. As disclosed above, a gas-permeable seal is created by layering a gas-permeable film, such as PDMS, in between two layers of perforated adhesive tape. Normally a bed of agar supplies the culture with humidity. In the devices of the present invention humidity and oxygen flow through the culture is controlled by PDMS, although other gas permeable films may function just as well.

FIG. 2 provides specific examples of the culture devices as described herein. FIG. 2D is a photograph showing the materials and equipment used to make the devices shown in FIG. 2E. These are cheap and readily accessible materials that can be used to make an effective portable culture device. As shown, the culture strips were made from scotch tape as the impermeable adhesive material. Patterned paper, together with bibulous paper pads made from blotting paper, was used to make the culture regions. The gas permeable membrane used in this example was PDMS. Circular holes were made in the scotch tape to which correspondingly sized, PDMS, patterned paper and paper pads were attached to make each culture strip. The paper pads were positioned between the PDMS membrane and the patterned paper to serve as a reservoir for water, aqueous culture media or other aqueous buffer or nutrient source during use. As shown in FIG. 2E, in this example, a single strip of scotch tape was used to form two culture strips by the use of a fold between the two culture strips. In order to close the device, the scotch tape was folded at the fold line such that the two culture regions contact one another at the inner paper layer. During use there is fluid communication and mixing between the two culture regions.

Figures 2A, 2B, 2C:
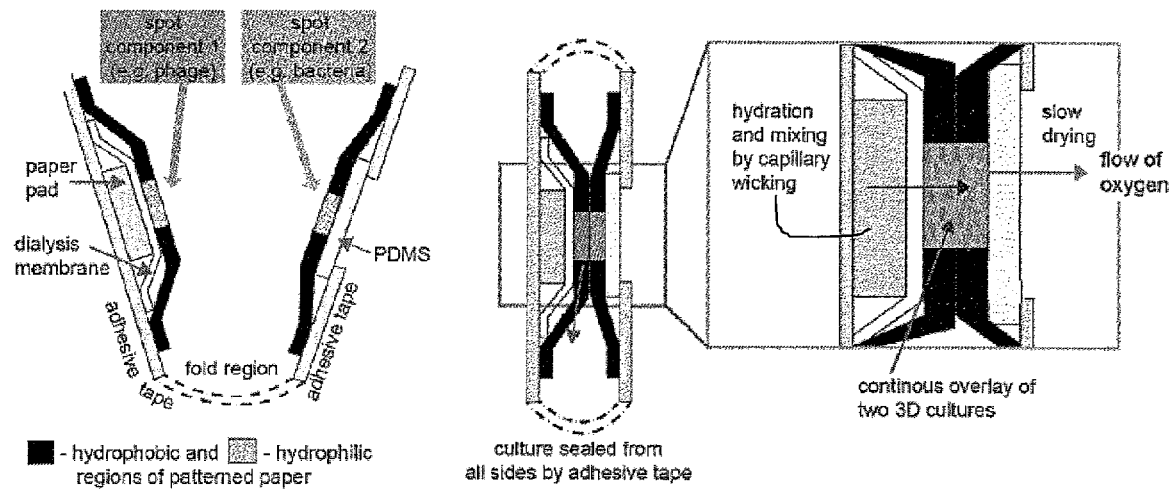
FIGS. 2A to C depict one embodiment of the culture device described herein device in an open condition (FIG. 2A) and a closed condition (FIG. 2B), with a detail of the culture pair shown in FIG. 2C.
Figure 2D:
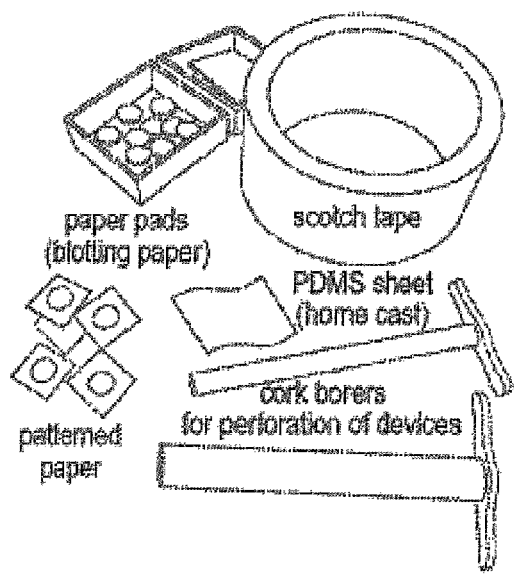
FIGS. 2D to F are drawings of examples of materials used to manufacture a culture device (FIG. 2D), a culture device made from the materials (FIG. 2E) and two culture devices made from the materials in closed and open conditions (FIG. 2F)
Figure 2E:
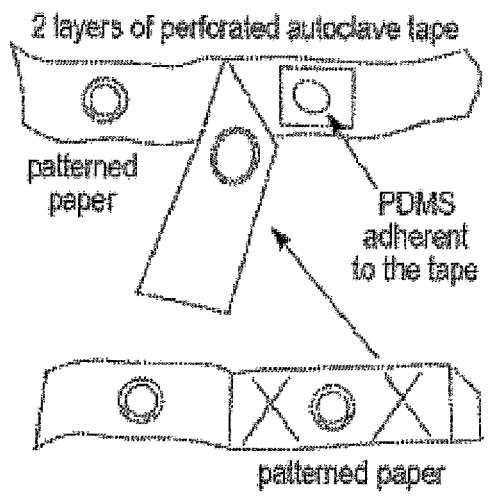
Figure 2F:
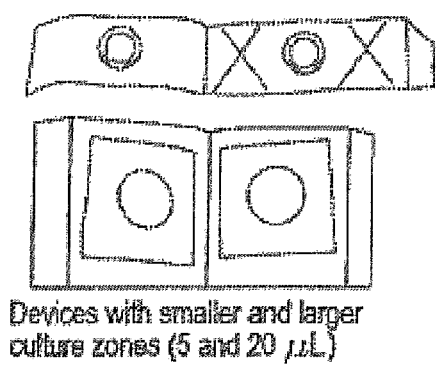

The photographs in FIG. 2F show examples of fully operational culture devices in an open state, which is used to load the bacteria and/or phage, and a closed state which is used for storage, transport and culturing.

Once made, the device can be autoclaved or otherwise sterilized for future use. In one example, the materials used to manufacture the device are presterilized and assembled under aseptic conditions to produce a sterile device. Alternatively, the materials are assembled and the device is subsequently sterilized, for example, by autoclaving or irradiation. Advantageously, in certain embodiments, the design of the device ensures sterility of the inner part of the device after sterilization. Contaminating microorganism cannot enter the sealed devices and devices remain sterile even if they are mishandled (stored on a dirty surface, stepped on, etc).

In a specific embodiment, the culture device includes at least two portions, each portion including multiple layers and constructed as follows using the components shown in FIG. 2. A 50 mm wide piece of adhesive tape, for example Scotch™ tape, is placed adhesive side up and a 10-15 mm hole is punched in the center of the tape, and then placed on a horizontal surface. A 20×20 mm sheet of polydimethylsiloxane (PDMS) is placed on top and over the hole so that the PDMS sheet seals to the adhesive side of the tape. PDMS sheets can be readily obtained in any thickness. In this example the PDMS sheet has a thickness of 1 mm, however, as would be readily appreciated, the thickness can be varied provided that the membrane permits oxygen to flow into the interior of the device. A 25×25 mm sheet of porous hydrophilic material, in the present example paper, which contains a liquid impervious substance on the outside perimeter edges to serve as a liquid impervious boarder and at least one culture zone or zones in the interior. The liquid impermeable substance can be any suitable hydrophobic material, for example a wax border. The wax containing zone seals to the adhesive outside of the PDMS sheet and the wax free zone(s) serves as a culture area/zone. The hydrophobic wax perimeter does not allow the liquid culture to wick into paper outside of the culture area as the wax-permeated border remains dry and sealed to adhesive tape for the duration of the incubation period. The amount of nutrient(s) can be increased or decreased depending on the thickness of the porous hydrophilic material. The thicker the porous hydrophilic material the greater amount of nutrients may be used. If even greater amounts of nutrients are required a paper pad may be placed under the porous hydrophilic material. The porous hydrophilic material is then covered with a second layer of single-sided tape with a 10-15 mm hole in the center adhesive side up, so that all of the layers are pressed together. Once the hole in top layer of tape is aligned with the bottom layer, this portion of the device is ready for use.

As would be readily appreciated by a worker skilled in the art, the specific dimensions referred to above are exemplary only and are not intended to be limiting. The dimensions of the culture regions, and the corresponding hole in the fluid impermeable material, can be varied significantly depending on various parameters, such as biological sample size, incubator size or availability, culture conditions, etc. In one example, the diameter of the culture regions is from about 1 mm to over 80 mm (the diameter of a standard petri dish). The materials used to manufacture the culture devices are selected, in part, based on the required size of the culture region. For example, culture devices having a larger diameter will require the use of relatively wide strips of fluid impermeable material.

Figure 4A:
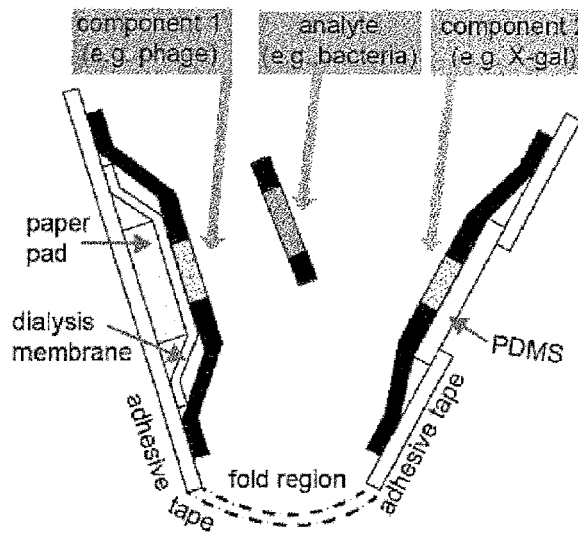
FIGS. 4A and B depict a multi-layer device incorporating additional layers inside the device.
Figure 4B:
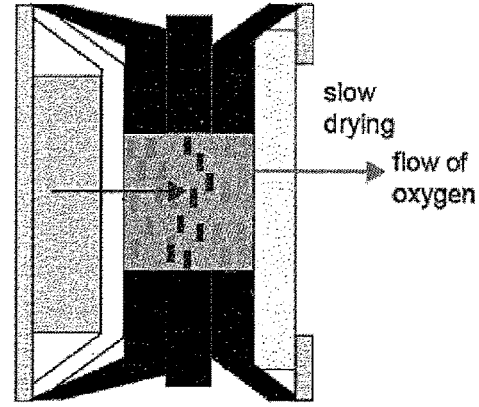

Following assembly, the culture regions of the device can then be loaded with an agarose solution, or other media, by spotting the solution onto the porous hydrophilic material. The agarose solution is then allowed to adsorb into the porous hydrophilic material and any excess solution is removed, for example, by shaking. The respective culture regions of each culture pair of the device are pressed and sealed together with the adhesive layers in a closed position. If necessary, the device is then sterilized, for example, by using an autoclave. After autoclaving, the device remains sterile until it is opened (FIG. 2B). Optionally, the device is formed with one or more additional culture regions placed between the two culture regions of each culture pair. In this example, culture regions are stacked together prior to autoclaving to form a multi-layered device (FIGS. 4A and 4B). Opening the device exposes at least two culture zones. If device was stored in the conditions that minimizes evaporation, such as in moisture impermeable containers, the devices contain sufficient amount of water and nutrients for the prolonged culture. If necessary, devices could be stored dry and then rehydrated with water or an aqueous solution, such as a buffer solution or a nutrient broth prior to culture. Once sufficient time has passed to allow the water or other aqueous solution to adsorb into the culture regions of the device any excess liquid is removed, for example, with shaking.

In accordance with one embodiment, the device is used to culture a microorganism, detect presence of viable microorganism in media with and without of antibiotic or detect microorganism with specific reporter gene. For example, a biological sample can be applied to one or both culture regions of a culture pair following hydration and incubated under conditions appropriate for the microorganism of interest. The culture conditions include temperature and culture media. For example, the culture medium can be selected to be permissive to growth of only certain bacterial types (e.g., gram negative or gram positive) or certain strains of bacteria (e.g., methicillin resistant). Such a system can be used to identify the presence or absence of a microbiological infection, such as a bacterial infection, in a subject.

Following addition of the bacteria, and bacteriophage, if used, the device is sealed and placed in an incubator at about 36° C. (or other temperature suitable for culture of the bacteria being cultured) for sufficient time to allow bacterial culture. If an incubator is not available incubation may conducted in any oven, for example a stove or cooking oven, or achieved by incubating the device next to human body, for example in a shirt or pants pocket. As demonstrated below humidification is not necessary for bacterial and bacteriophage culture, but it is preferred.

In the example shown in FIGS. 2A to 2C, the device additionally includes a bibulous paper pad in a first culture region. The other culture region of the culture pair does not include a paper pad. The paper pad is used as a reservoir for water, aqueous culture media or other aqueous buffer or nutrient source to assist in maintaining hydration during use. This example also includes a dialysis membrane between the paper pad and the porous hydrophilic material of first culture regions. Dialysis membrane in general is not necessary and provides only a small advantage for culture (reduced loss of water over time). As also shown in FIGS. 2A to 2C, the first culture region does not include a gas permeable membrane. With this arrangement, the water from the paper pad is wicked through the first porous hydrophilic material, carrying with it components previously applied to the first culture region (e.g., bacteriophage). These components then mix with the components (e.g., bacteria and components from the biological sample) on the second culture region as the water is wicked to the second porous hydrophilic material.

Mixing is achieved by bringing two or more pieces of porous material in contact with each other. If thickness of the porous material is small, rapid mixing of reagents is achieved by diffusion. For example, using filter paper with a thickness of 200 µm, diffusion of the liquid across the paper occurs within minutes.

Figure 3A:
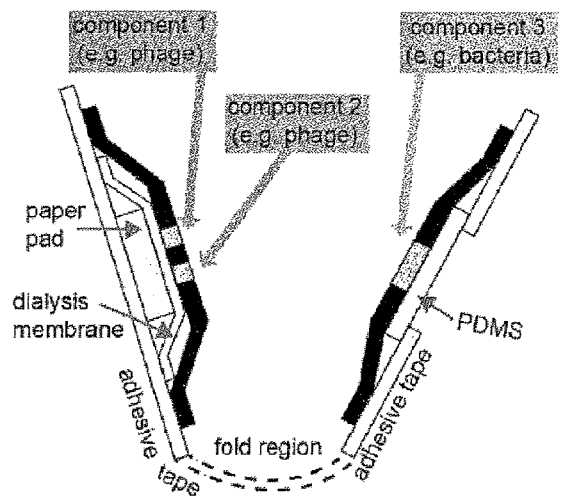
FIGS. 3A and B depict a multi-zone assays device with patterned porous hydrophilic material in multiple zones to run parallel assays in the device.
Figure 3B:
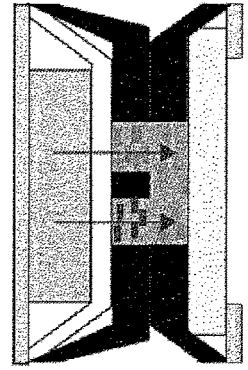

A multi-zone culture device is shown in FIG. 3. Using paper patterned in multiple zones parallel assays may be run in the device. For example to two different phage (component 1) and (component 2) constructed to recognize two different analytes in the presence of a bacteria (component 3) (FIG. 3A). In this device, multiple hydrophilic zones may be printed or constructed instead of a single hydrophilic zone. Each hydrophilic zone may be isolated from one another and different analytes, different reagents or different bacteria can be cultured in these zones as depicted in the parallel overlay culture in FIG. 3B.

In another embodiment the culture device can be constructed to have multiple layers as depicted in FIGS. 4A and 4B. Incorporation of additional layers inside a multi-layer device facilitates introduction of multiple analytes, reagents, or provides the ability to conduct complex co-culture assays.

In another embodiment, porous hydrophilic material can be divided into reagent-containing areas and fold areas. In another embodiment, porous hydrophilic material may be cut in separate areas of defined size and placed on top of flexible substrate, which can then be folded. Accordingly, by using specific folding several sheets of porous hydrophilic material, and reagents stored on the porous hydrophilic material may be brought into contact with each other. In one embodiment the porous hydrophilic material is configured in an X-shaped pattern with a spot of analyte (pIII) in the center and (1) bacteria (2) phage (3) lysis buffer and (4) luciferin on four arms. Sequential folding/unfolding of the four arms runs the multi-step assay. The contact can be maintained either mechanically with clips or holders or chemically using adhesive tape for a sufficient period of time so that the reaction/infection may be amplified. A device made entirely of paper and adhesive tape, can be folded and unfolded reversibly, thus, mixing a desired reagent(s) in a step wise manner to control the reaction as required.

Various studies have been performed, some of which are detailed in the Examples below, to evaluate the ability of the culture devices to support bacterial growth and bacteriophage infectivity and propagation. The results of these studies show that the culture device can be produced at low cost using components commonly found on site in areas of the world in which resources are sparse or limited. Moreover, the device functions well as a diagnostic tool in many different environments, for example those having low humidity, high humidity and even in environments which may be low in oxygen. Therefore, the culture device is suitable for use in the field or point-of-care developing countries, where resources such as electricity, electronic components, liquids (water), reagents that require refrigeration, incubators and the like are not available.

Assay using the Culture Device

In accordance with a specific aspect, there is provided a diagnostic assay using the above described culture device for identifying the presence, or quantifying the amount, of an antibody, antigen or analyte in a biological sample. In this assay, following hydration of the culture regions of the device, at least one culture region is loaded with dormant phage and at least one other culture region is spotted with bacteria in solution, such that each culture pair includes a culture region loaded with dormant phage and a corresponding culture region loaded with bacteria. Closing and sealing the device brings the phage and bacteria in contact and initiates mixture of the bacteria and phage (FIGS. 2 to 4) through fluid communication of the culture regions in the culture pair. As described in more detail below, the dormant phage can be activated to become infective, for example, by the presence of an antibody, analyte or antigen within a biological sample applied to the device. Following infection, the phage can rapidly replicate in the host bacteria. Detection of the replicated phage is indicative of the presence of the antibody, analyte or antigen of interest.

In use, the culture device is opened (FIG. 2A), hydrated, dormant phage and bacteria are separately spotted on the device, a biological sample is added and the device is sealed (FIG. 2B) on all sides with the impermeable adhesive material. Hydration and mixing of the reactants is run to completion through capillary wicking (FIG. 2C) of liquid as a result of the continuous overlay of at least two culture regions. The gas permeable membrane allows the device to remain hydrated by maintaining moisture within the device, while also permitting a continuous flow of oxygen to the interior of the device.

In order to detect an analyte of interest a binding assay requires a molecule that specifically recognizes the analyte. Many assays use antibodies or biomolecules such as peptides or aptamers that have similar binding properties for detecting an analyte of interest. Production of these molecules, however, requires advanced infrastructure to properly conduct cell culturing and protein purification. The assays described herein use genetically and/or chemically modified bacteriophage instead of antibodies or other binding molecules.

Bacteriophages, unlike biomolecules, can amplify in simple bacterial culture. This ability makes them ideal for on-site production. Solutions of bacteriophages can be obtained simply by sedimentation of the raw bacterial culture at ~3000 G. There are several simple devices that can induce this sedimentation. Bacterial culture that produces phage can be grown in any environment that has reasonable temperature-control capabilities (e.g., oven). Although bacteria culture requires a sterile component, this sterilization can be obtained using a very simple setup.

The present culture assay takes advantage of the natural ability of a bacteriophage to produce multiple copies of itself in a host bacterial cell. Delivery of a genetically modified phage genome to infected bacteria produces many copies of phage, which then go on to infect more bacteria. Introducing even one phage into a large population of bacteria, e.g., $1 \times 10^9$ bacteria, produces a large number of phage, up to $100 \times 10^{11}$ to $1 \times 10^{12}$ or more. This phage amplification is rapid.

Infection, on its own, is not suitable for a diagnostic method, because it happens whenever phage and bacteria are mixed together. To make it useful as a diagnostic, this natural infection and amplification must be enhanced and engineered to occur in the presence of a specific analyte of interest. The present assay takes advantage of dormant phage and bacteria. Dormant phage clone does not infect bacteria until it is activated by mixing with a specific molecule or analyte. Once an analyte is introduced, the present assay promotes binding of the analyte to phage, which in turn activates the phage to become infective. Active phage can then infect bacteria and produce a large number of phage, which amplifies the analyte signal so that it can be detected.

For example, it is well known that infection of bacteria by phage can be accompanied by a visible readout if phage infection delivers a specific reporter gene to bacteria, for example the β-galactosidase gene (lacZ) or the luciferase gene. If the phage genome contains a reporter gene for fluorescent or luminescent protein, then infection of bacteria by such phage produces copies of the fluorescent or luminescent protein or the enzyme. If phage contains a gene for an enzymatically active protein, its infection produces bacteria with novel enzymatic function, such as the ability to process colorimetric substrates, which are measurable. Similar technology works for any viral-host system.

This property works best for non-lytic phages that infect a bacterial host cell without disturbing the viability of host. If phage or virus is lytic, such a read-out will work if the gene that is delivered is expressed as fast as the phage or viral proteins. Fluorescent, luminescent or enzymatically active proteins must become active before the host is destroyed by lysis.

One example of the diagnostic assay of the present invention exhibits the following characteristics:
(1) It contains large amounts of dormant phage and bacteria stored separately in a simple portable culture device as described above. The dormant phage and bacteria are kept separate from each other in the culture device until mixing occurs. Folding the culture device mixes dormant phage with bacteria, however, this mixing produces no infection and no visible signal at this stage;
(2) Mixing of dormant phage and bacteria with a sample can produce one of two outcomes:
   a. If the specific molecule of interest (e.g., analyte) is present in the sample, it binds to dormant phage, activating the phage, which produces at least one infection event. This event produces more infective phage particles that rapidly infect the whole population of bacteria in the mixture producing a detectable signal; or
   b. If the sample does not contain the specific molecule of interest (e.g., analyte), the phage remains dormant and, therefore, cannot infect the bacteria in the mixture and cannot produce a visible signal.

Dormant phage used in the present culture assay carry a reporter gene and have two characteristics: (1) dormant phage cannot infect bacteria if the target substance is not present in the same assay solution (dormant phage becomes infective only when the target substance binds to it); and (2) entry of "activated dormant phage" into bacteria produces constitutively active phage that can infect bacteria in the absence of further target substance as the infective bacteria can express the reporter gene to allow detection of infected bacteria indicative of the presence of the target substance.

The infective process from dormant phage to activated phage to infected bacteria with production of more phage is termed avalanche analyte-triggered infection (AATI), because it can yield a large number of infective phage and a continuous sequence of infection-production-reinfection events from a single molecular binding event.

Natural bacteriophages (phages) or viruses contain coat proteins and DNA that encodes the sequences of these proteins. Some coat proteins of phage are involved in infection. Integrity of these proteins is necessary for infection of bacteria. These coat proteins are referred to herein as coat proteins involved in infection (CPIII). Genetic deletion of portions of the CPIII renders phage non infective.

It is well known that in some phage and viruses, CPIII have two distinct domains. Genetic deletion of one domain makes phage non-infective. Assembly of CPIII from two domains in vitro, can restore infectivity of phage. For example, in phage M13, protein pIII is involved in the infection process. This protein has an N-terminal domain (NT) and a C-terminal domain. Deletion of N-terminal domain results in the phage particle becoming non-infective. Phage with CT alone, abbreviated as "CT-phage", is non infective. However, covalent or non-covalent binding of NT to CT-phage in vitro restores infectivity of phage. This technology which has been described above is termed "selectively infective phage" (SIP).

SIP has been used to detect the interaction between two molecules termed molecule (1) and molecule (2) immobilized on NT and CT, respectively. This process is described in the following sequence:
NT-1+2-CT-Phage (non infective)→NT-1:2-CT-phage (infective)

This technology is used to detect binding between molecules covalently linked to CT and NT. Binding of two molecules is translated into an event (bacterial infection), which can be easily detected and amplified. This technology, however, cannot be used with a diagnostic assay because it only works when molecules 1 and 2 are covalently attached to phage proteins. Moreover, although the phage infects the bacteria, the progeny phage is non-infective. Diagnostic assays require detection of analytes present in solution. Described herein is a different construct that can be used to detect a soluble analyte, according to the following sequence:
NT-1+analyte+2-CT-phage (non infective)→NT-1:AN:2-CT-phage (infective)

This sequence of events indicates non-covalent interaction between the analyte and molecule 1, or non-covalent interaction between analyte and molecule 2. Molecules 1 and 2 are able to bind to the analyte of interest at two distinct binding sites. It is conceptually different from SIP technology, because it requires a step of designing two independent ligands to detect an analyte of interest, making this technology well suited for use in a diagnostic assay. This technology can be modified to detect any analyte of interest, for which two distinct ligands can be found. This technology is referred to as analyte-triggered infection (ATI).

Design and Production of Phage Construct for AATI

Described herein is one example of an engineered AATI bacteriophage, which (1) contains incomplete coat proteins involved in infection, and hence cannot infect a bacterial host; and (2) contains the genome of complete coat protein, and hence can produce infectious particle once the genome of the bacteriophage or virus is delivered to the host bacterial cell.

Figure 14:
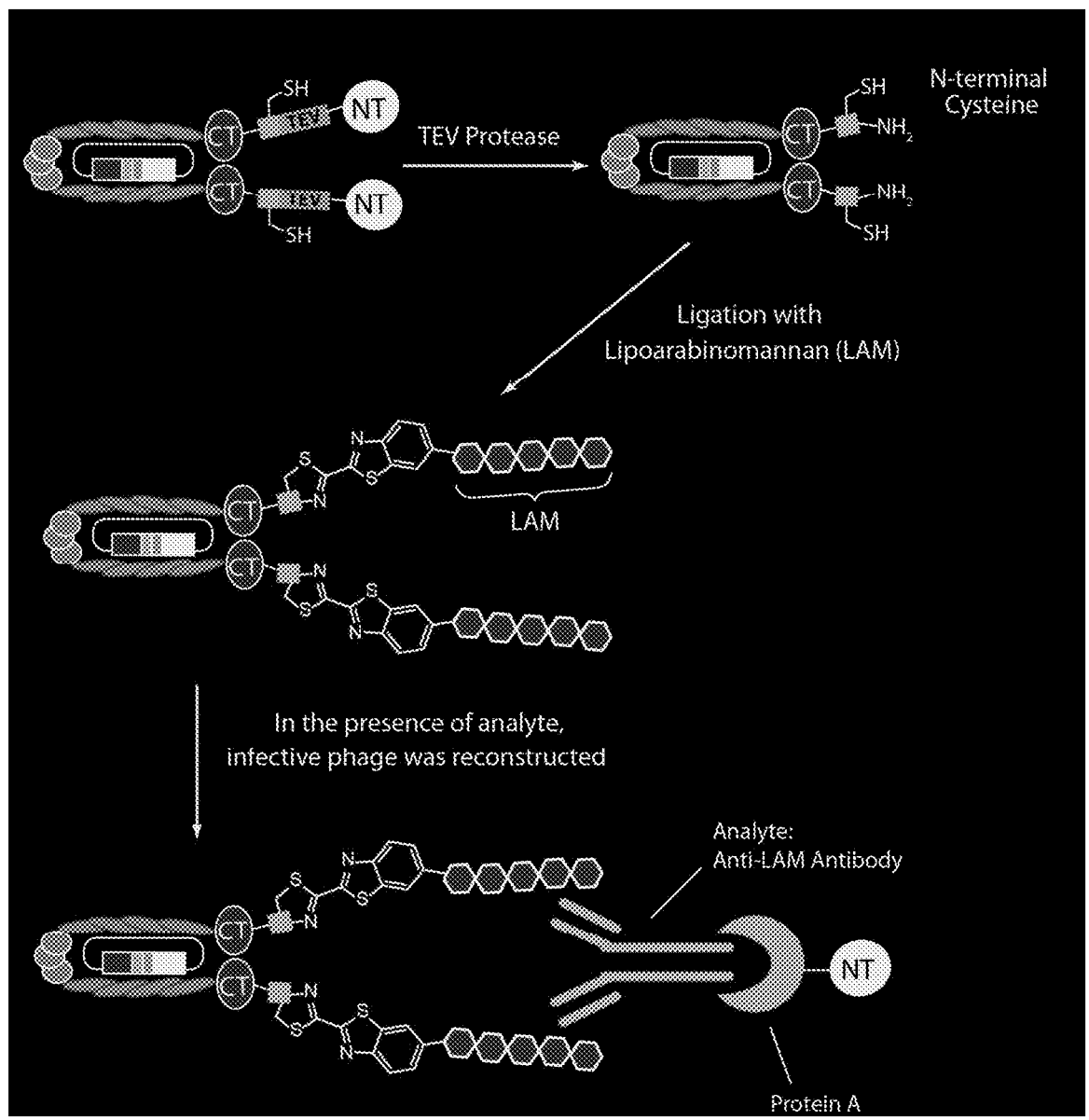
FIG. 14 depicts a chemical post-translational modification of the CT domain resulting from TEV protease cleavage.

Such hybrid phage is produced by post-translational modification of infective phage. In one embodiment, this modification is cleavage of pIII protein into NT and CT fragments by the action of specific protease (FIG. 14). This cleavage produces soluble protein NT and non-infective phage-CT, which, nevertheless contains "infective genome". As described above, phage-CT can be converted to "dormant phage", which will infect bacteria only when bound to an analyte of interest. This infection will deliver "infective genome" to bacteria and produce viable phage that can continue amplification in the absence of any further analyte, thus exhibiting avalanche analyte-triggered infection (AATI).

Figure 12A:
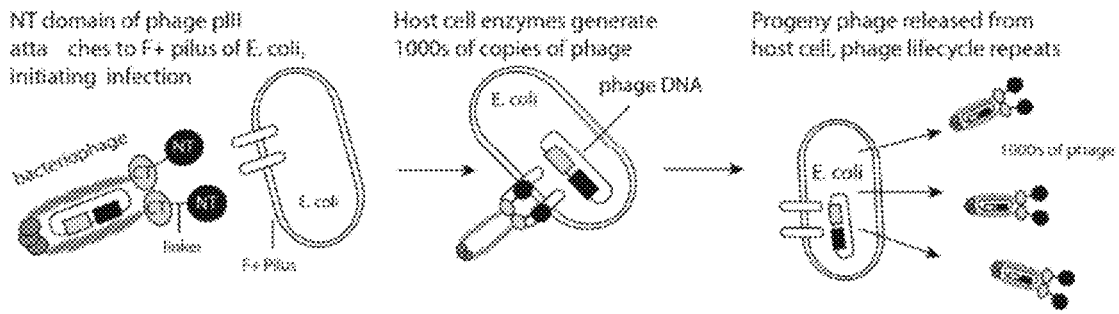
FIGS. 12A-12C illustrate wild-type phage infection (FIG. 12A), infection by selectively infective phage (FIG. 12B) and the design and production of phage construct for the avalanche analyte-triggered infection (AATI) technology (FIG. 12C)
Figure 12B:
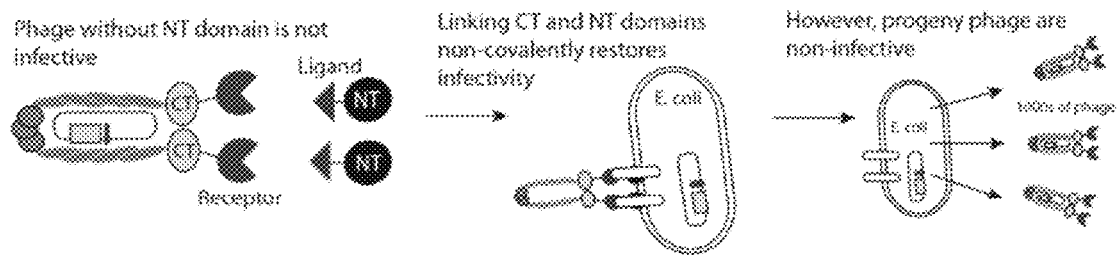

It is well known that wild type phage infect its host (bacteria) at any time simply by being brought in contact with the host (FIG. 12A). Contrary to this, selectively infective phage (SIP), as shown in FIG. 12B, in which the N-terminal domain is deleted by way of genetic manipulation cannot infect its host. SIP are only able to infect bacteria in the presence of N-terminal domain, by binding to N-terminal domain non-covalently. Infection of bacteria by SIP produces more SIP which are only able to infect bacteria if more N-terminal domain is present. More importantly, however, SIP do not produce progeny that are infective.

Figure 12C:
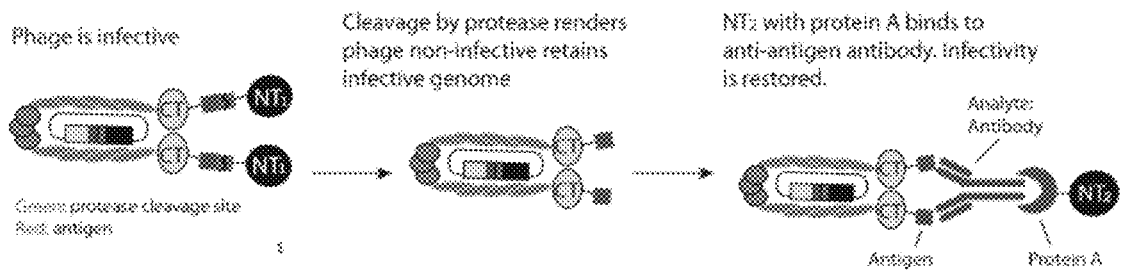

In the present system, AATI phage is non-infective because it also lacks N-terminal domain of pIII. AATI phage, however, contains infective genome. This system can be manipulated to detect any antibody, antigen or analyte, even at very low levels, because the system is able to rapidly amplify signal for detection of the antigen through AATI. AATI phage is made infective by adding an antibody that recognizes the antigen and adding a molecule that binds to antibody, in the example depicted in FIG. 12C the molecule is protein A, which is able to readily fuse to an N-terminal domain. The system is suitable for any peptidic antigen, because any peptide can be encoded with a linker molecule. The system is also suitable for incorporation of non-peptidic antigen because proteolytic cleavage exposes a unique modification site, N-terminal serine, which can be regioselectively oxidized to yield an aldehyde and modified with any aldehyde-reactive molecule, such as carbohydrate with a hydroxylamine linker.

Steps for production of fusion of protein A and N-terminal domain of pIII are described in the Examples below. They are simple and can be done from two genes for two proteins (for example, pIII and protein A) by any person skilled in the art. Certain embodiments employ conventional techniques of molecular biology (including recombinant techniques), microbiology, cell biology, biochemistry, and immunology, which are known to those of ordinary skill of the art. Such techniques are described in, e.g., "Molecular Cloning: A Laboratory Manual", third edition (Sambrook et al, 2001); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Figure 13:
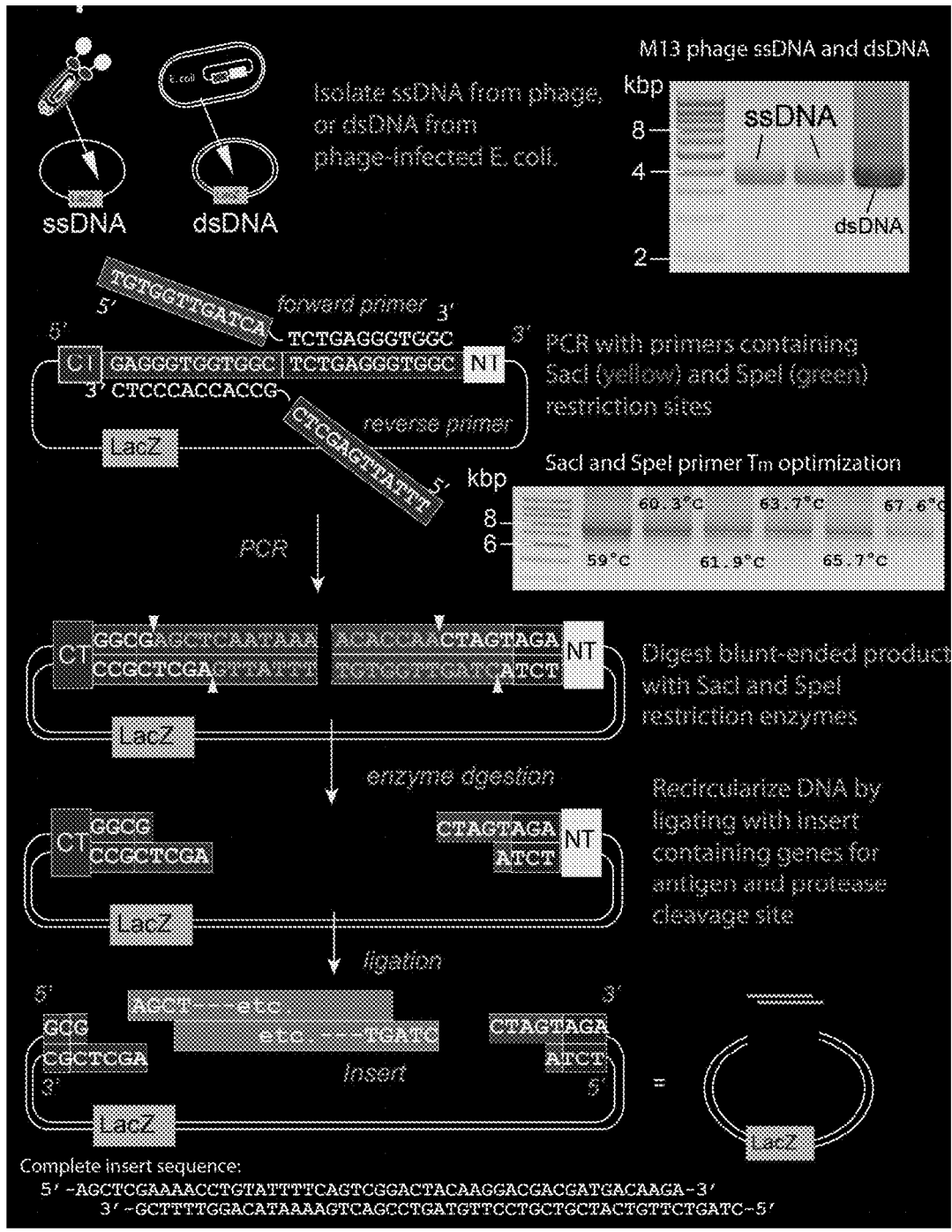
FIG. 13 shows an example of the preparation of AATI constructs from a wild type M13 bacteriophage; including a portion of the sequence of M13 phage (SEQ ID NO.: 2), a forward primer (SEQ ID NO.: 3), a reverse primer (SEQ ID NO.: 4), complete insert sequence (SEQ ID NO.: 5), complete insert sequence—reverse (SEQ ID NO.: 6), and a filamentous M13 phage carrying a LacZ reporter gene on pIII protein (SEQ ID NO.: 7)

FIG. 13 schematically details the steps for the preparation of AATI constructs from a wild type M13 bacteriophage. PCR amplification, using wild-type genome as template, generates linear genome with additional sequences. Optimization of PCR conditions is shown.

Enzyme digestion and ligation with an insert sequence re-circularizes the genome of phage and yields phage that contains an enzyme cleavable linker and an antibody-recognition site, in this example pIII protein. Phage produced from this DNA can be treated with TEV protease to cleave the N-terminal domain. As depicted, the phage encodes a FLAG recognition sequence, which would recruit a model anti-FLAG antibody to a phage. This phage, therefore, can detect anti-FLAG antibody. This is but one example as any other peptide antigen can be encoded genetically in an identical manner for use with the present diagnostic assay.

Non-peptidic antigen, such as the carbohydrate lipoarabinomannan (LAM) from the cell wall of M. tuberculosis can be easily introduced onto the phage by chemical modification of the N-terminal Cys resulting from cleavage by Tobacco Etch Virus (TEV) protease (FIG. 14). This modified phage then becomes sensitive to the presence of anti-LAM antibody. As such the assay system of the present invention may be used as a diagnostic to detect TB infection. It is well within the skill of the artisan to make other modifications, which may include chemical oxidation of N-terminal Ser or Thr and ligation of hydrazine or hydroxylamine-containing LAM (or other molecules) to the resulting N-terminal aldehyde. These examples demonstrate detection of antibodies, which may be used to detect antigens in many different diseases or disorders, for example, HIV and malaria. The assay system of the present invention may also be modified to detect more than one analyte. Other components that can be fused to CT-phage and the N-terminal domain include, but not limited to: any protein with two binding sites and DNA strands, which can be brought together by a longer complementary strand.

To gain a better understanding of the invention described herein, the following examples are set forth. It should be understood that these examples are for illustrative purposes only. Therefore, they should not limit the scope of this invention in any way.

EXAMPLES

Example 1

Calibration of Culture Device

Figure 5:
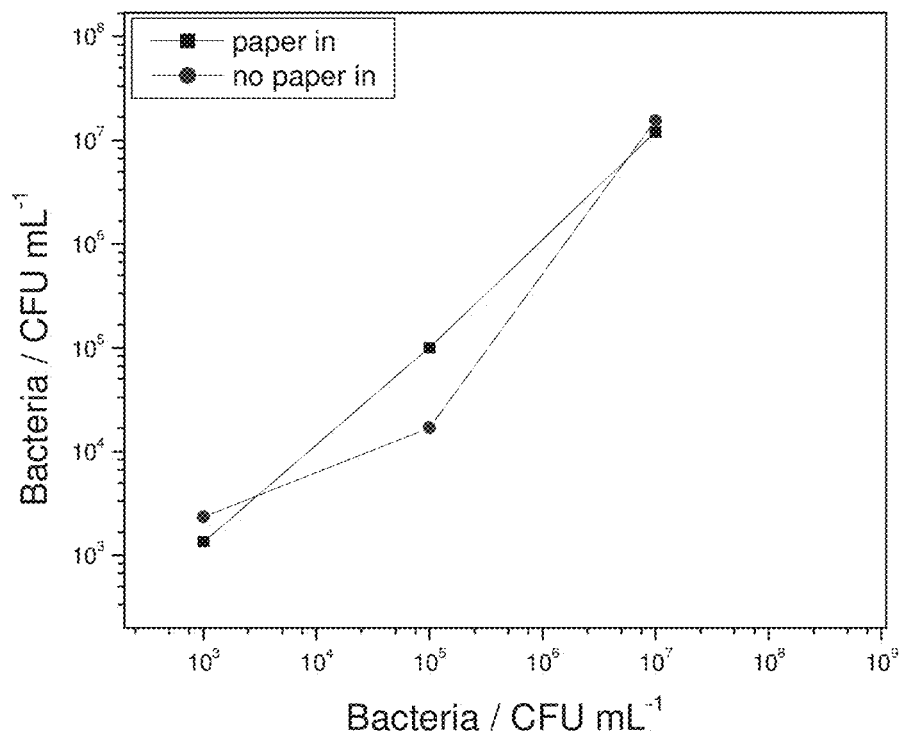
FIG. 5 depicts a graph of the calibration of bacteria counts in the devices.

In this Example, *E. coli* in 10 μL of Luria-Bertani ("LB") media was spotted on the porous hydrophilic material and immediately extracted and vortexed in excess of LB media. The number of bacteria in the extracted solution was estimated by counting and quantifying colony forming units (CFUs) or plaque forming units (PFUs). The performance of the device was evaluated by opening the device at specific time points and removing the culture region portion of the porous hydrophilic material for analysis. The results of this calibration are provided in FIG. 5. The calibration of bacterial growth was conducted using a piece of paper as porous hydrophilic material in the device and 10 μL of *E. coli* $1\times10^5$ cfu $mL^{-1}$ mixed with 5 mL of LB media. A second calibration was done without paper and 10 μL of *E. coli* $1\times10^5$ cfu $mL^{-1}$ in 5 mL of LB media. Both were incubated to 37° C. As expected, bacterial growth using porous hydrophilic material was found to be superior to growth in the absence of a suitable substrate (FIG. 5), as determined by the linear calibration curve.

These results further demonstrate that the present culture devices can be easily calibrated.

Example 2

Comparison of Culture Conditions

Various culture conditions were tested to demonstrate the ability to culture bacteria and bacteriophage under conditions experienced in the culture devices described herein.

Bacterial Culture Conditions

First, a study was performed to compare growth of bacteria in a piece of porous hydrophilic material on the surface of an agar plate to the growth of bacteria on porous hydrophilic material soaked with agar and covered with PDMS. The results are shown in FIG. 6B.

Figure 6A:
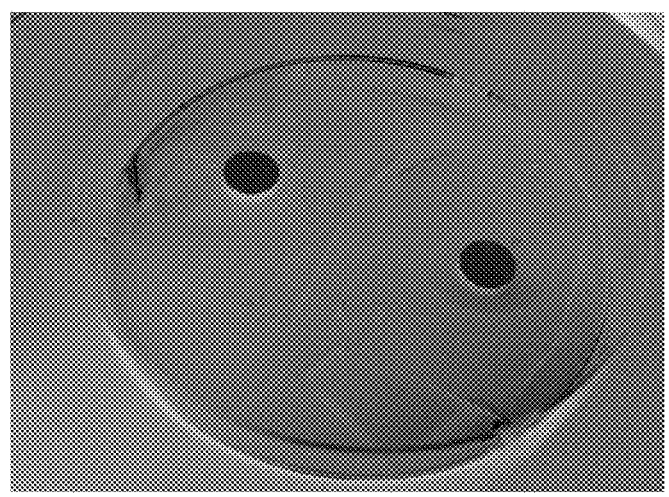
FIG. 6A is a comparison of the growth of bacteria in paper on the surface of an agar plate (left) versus growth of bacteria soaked on paper with agar and covered with PDMS (right)

A piece of porous hydrophilic material was with treated with 10 μL of *E. coli* $1\times10^5$ cfu/mL and placed on agar. In comparison, three pieces of porous hydrophilic material were prepared, as follows: i) one layer topped with agar in porous hydrophilic material+one layer with bacteria in porous hydrophilic material 10 μL+ and another layer topped with agar in porous hydrophilic material all of which are covered with a PDMS layer. These mixtures were incubated in an empty petri dish as shown in FIG. 6A. Both experiments were incubated to different times and quantified by titration in 5 mL of LB media. Bacteria were grown using LB agar media and incubated at 37° C.

Figure 6B:
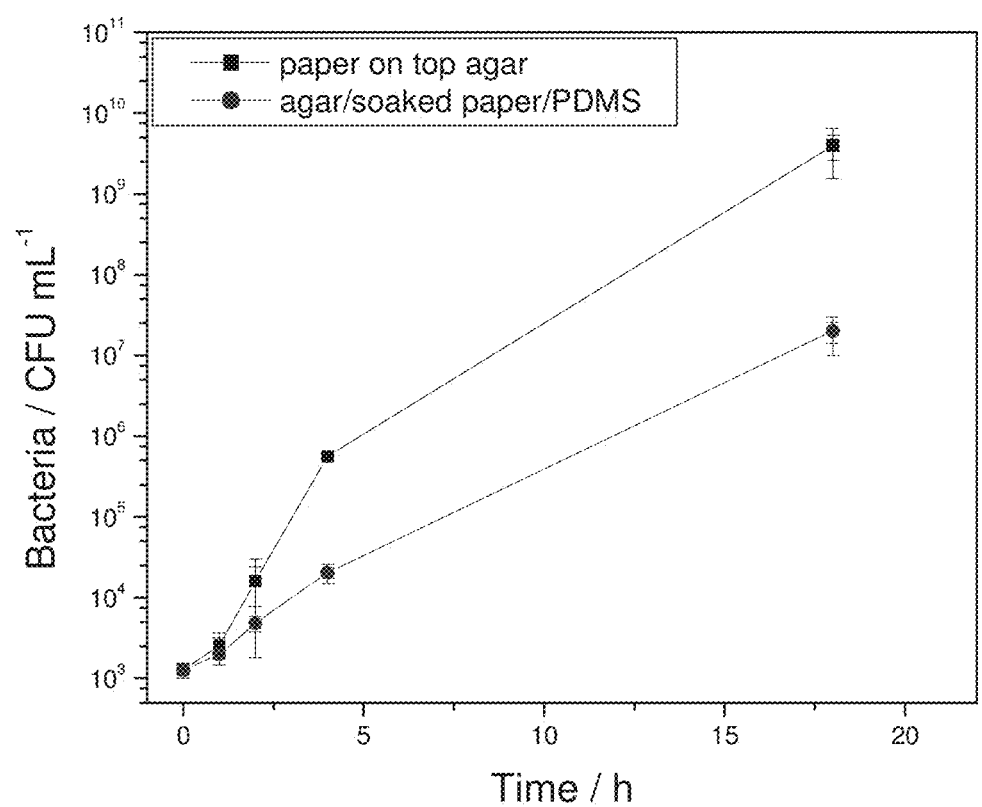
FIG. 6B is a graph showing the growth of $E.\ coli$ bacteria measured in colony forming units/ml of FIG. 6A.

The results of this study show that growth of bacteria in the culture devices is very similar to growth of bacteria on agar (FIG. 6B).

Bacteriophage Infectivity and Culture

Figure 7:
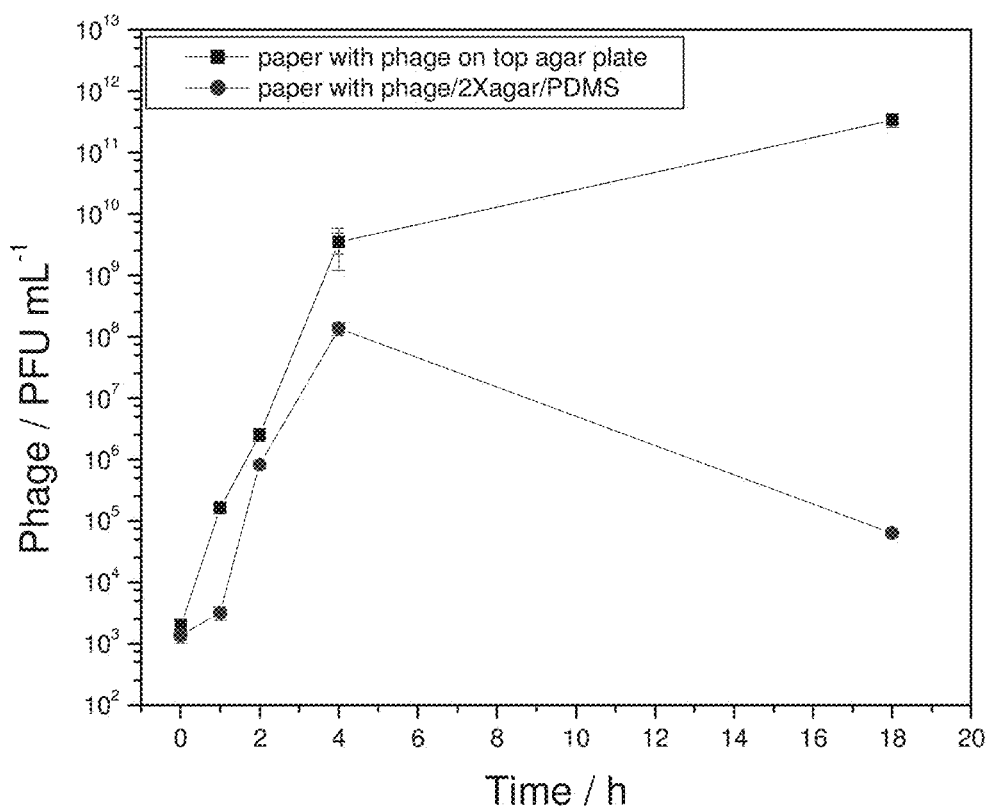
FIG. 7 is a graph of the phage infection of $E.\ coli$ in paper on the surface of an agar plate versus phage infection of $E.\ coli$ soaked on paper with agar and covered with PDMS.

Second, a study was performed to compare phage infection on a piece of porous hydrophilic material (paper) on the surface of an agar plate to phage infection using phage in and on a porous hydrophilic material soaked with agar and covered with PDMS. The results are shown in FIG. 7.

A piece of porous hydrophilic material was treated with 10 µL of E. coli overnight and with 10 µL of phage to $1\times10^5$ pfu mL$^{-1}$ on the surface of agar plate. In comparison, four pieces of porous hydrophilic material; one layer soaked on top with agar 10 µL+one layer spotted with 10 µL of E. coli overnight+one layer spotted with 10 µL of phage to $1\times10^5$ pfu mL$^{-1}$+another layer soaked on top with agar 10 µL, were covered with a PDMS layer. This arrangement was incubated in an empty petri dish. Both experiments were incubated to different times and quantified by titration in 5 mL of LB media. Phage were grown using LB agar media with X-gal and incubated to 37° C.

Without wishing to be bound by theory, the reduction of phage PFUs after overnight incubation and reduction in growth observed from the incubation using paper only was likely caused by drying of thin sheets of paper. Reduction of the volume of nutrient-containing medium increased the rate of evaporation. This evaporation problem was circumvented by sandwiching the paper between sheets of gas permeable material (PDMS). Increasing the thickness of the paper also mitigates this problem as does the use of a paper pad and/or a dialysis membrane as shown and described above and in FIGS. 2 to 4.

Bacterial Culture in a Culture Device

Figure 8:
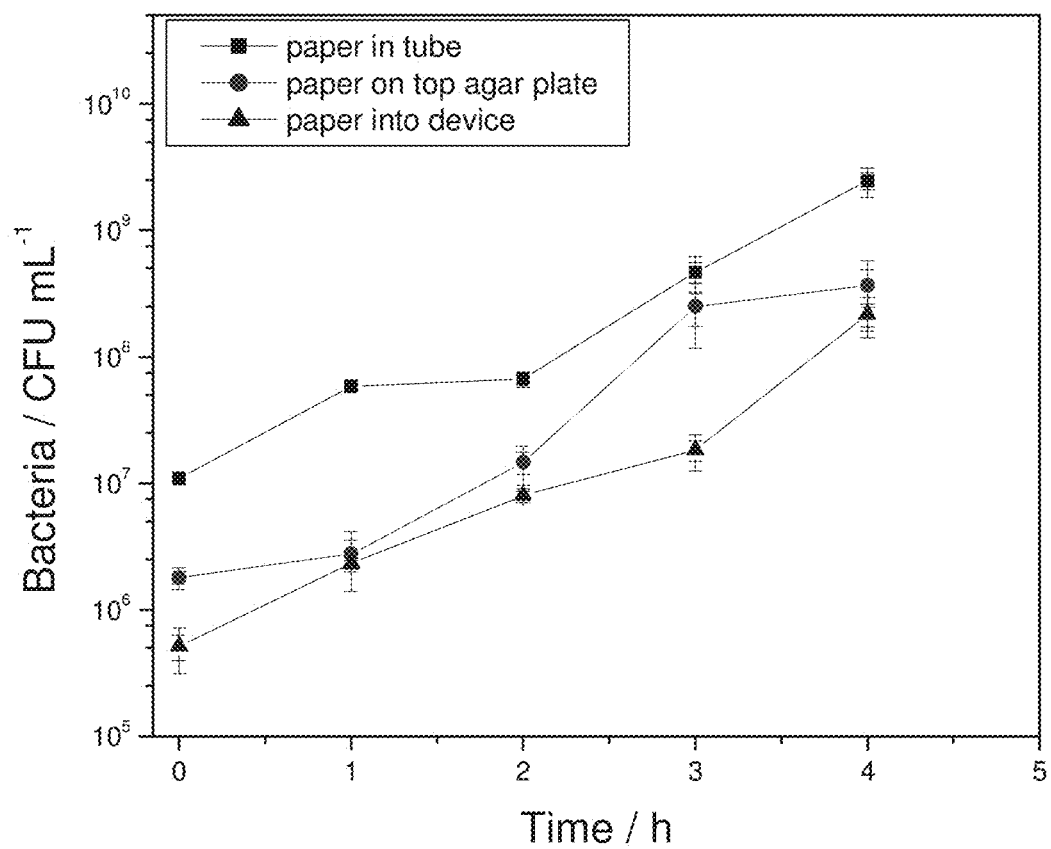
FIG. 8 shows a comparison of the growth of bacteria (1) in a piece of paper dropped into a shaking culture ("paper on tube"), (2) in paper on top of agar and (3) in devices containing bacteria in paper on top of paper soaked with agar covered by polydimethylsiloxane (PDMS)

Third, a further comparison of growth of bacteria under different conditions was performed. Bacterial growth was assessed in (1) paper dropped into a shaking culture ("paper on tube"), (2) in paper placed on top of agar, and (3) in culture devices containing bacteria in paper on top of paper soaked with agar covered with polydimethylsiloxane (PDMS). The results are shown in FIG. 8.

A piece of porous hydrophilic material with 15 µL of E. coli was incubated overnight with a piece of porous hydrophilic material with 15 µL of phage to $1\times10^5$ pfu mL$^{-1}$ placed into a tube with 5 mL of LB media. Another a piece of porous hydrophilic material with 15 µL of E. coli was incubated overnight with a piece of porous hydrophilic material with 15 µL of phage to $1\times10^5$ pfu mL$^{-1}$ on the surface of an agar plate. In a third system a disposable/portable culture device was made, as described herein, using adhesive tape and two folds with layers of PDMS, sponge (paper pad), a dialysis filter and piece of porous hydrophilic material (15 mm). Both culture regions of the device were dropped with 30 µL of agar on top and then autoclaved. Then, one culture region of the device was inoculated with 15 µL of E. coli incubated overnight and the other culture region was spotted with 15 µL of phage to $1\times10^5$ pfu mL$^{-1}$. Each of the three systems were incubated to different times and then quantified by titration in 5 mL of LB media with the layer of porous hydrophilic material and sponge from the device. Bacteria were grown using LB agar media with X-gal and incubated to 37° C.

All three systems demonstrated successful bacterial growth. Bacterial growth rate was found to be lower using the culture device than using either a shaken culture or culture on agar, however, the slower growth rate does not influence phage production. Since growth of bacteria in the culture device is not limited by water or oxygen, bacterial growth can easily be improved by adjusting the level of nutrients in the system.

Bacteriophage Culture in a Culture Device

Figure 9:
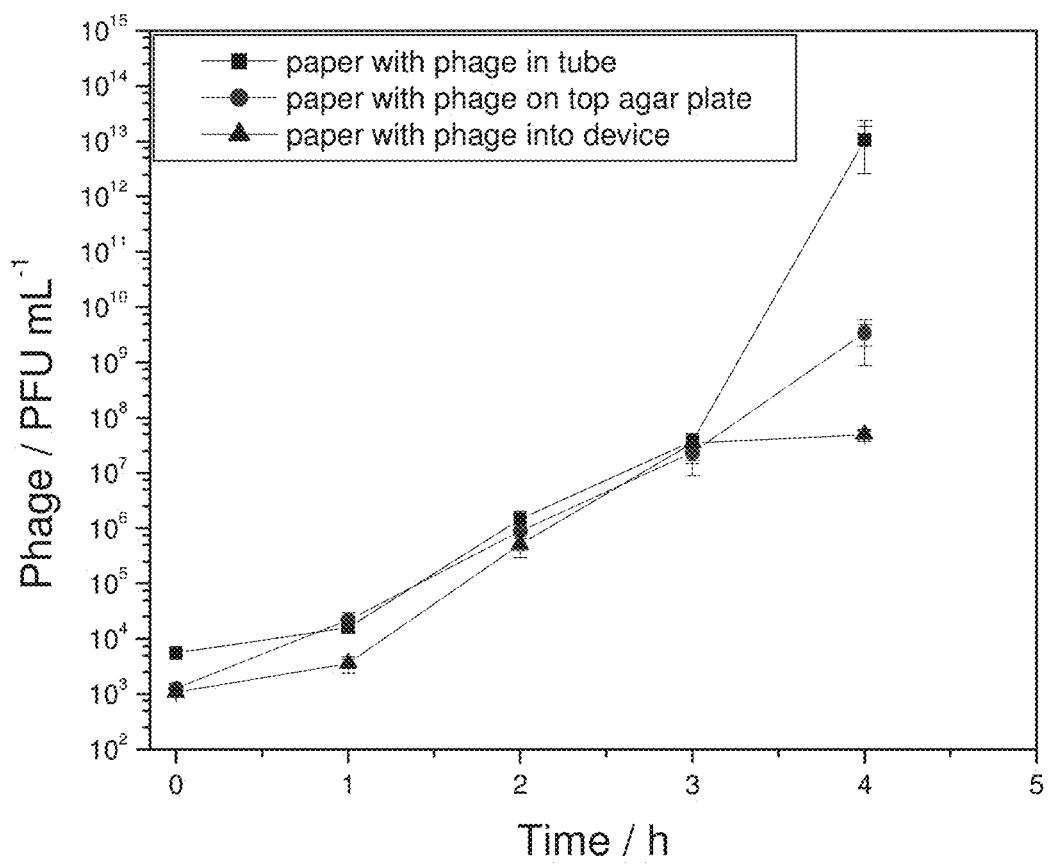
FIG. 9 shows a comparison of phage infection of bacteria (1) in a piece of paper dropped into a shaking culture, (2) in paper on top of agar and (3) in devices containing bacteria in paper on top of paper soaked with agar covered by PDMS.

Fourth, bacteriophage infection and amplification in bacteria was assessed using a culture device as described herein and compared to systems in which the bacteriophage infection and amplification was performed using (1) paper dropped into a shaking culture ("paper in tube"), and (2) paper placed on top of agar. The results are shown in FIG. 9.

A piece of porous hydrophilic material spotted with 15 µL of E. coli was incubated overnight with a piece of porous hydrophilic material spotted with 15 µL of phage to $1\times10^5$ pfu mL$^{-1}$ in a tube with 5 mL of LB media. Another piece of porous hydrophilic material spotted with 15 µL of E. coli was incubated overnight with a piece of porous hydrophilic material spotted with 15 µL of phage to $1\times10^5$ pfu mL$^{-1}$ on the surface of an agar plate. In a third system a disposable/portable culture device was made, as described herein, using adhesive tape and two folds with layers of PDMS, sponge (paper pad), a dialysis filter and piece of porous hydrophilic material (15 mm). Both culture regions of device were dropped with 30 µL of agar on top and then autoclaved. Then, one culture region of the device was inoculated with 15 µL of E. coli incubated overnight and the other culture region was spotted with 15 µL of phage to $1\times10^5$ pfu mL$^{-1}$. Each of the three systems was incubated to different times and then quantified by titration in 5 mL of LB media with the layer of porous hydrophilic material and sponge from the device. Phages were grown using LB agar media with X-gal and incubated to 37° C.

Layering of two sheets, one with phage and one with bacteria on top of a layer of agar, lead to rapid infection and production of phage progeny. The rate of production in the two-layer culture was similar to that of phage infection in shaking culture (paper in tube). Although growth of bacteria was reduced or slower in the device (see FIG. 8), the rate of infective phage production in the first 3 hours is similar to that in the controls, i.e., shaking culture and that in the layers of paper on top of agar dish. Therefore, a rapid infection and production of phage progeny is possible using the culture device described herein.

Culture Conditions within Culture Device

Growth of bacteria and phage infection and production is affected by three main criteria: oxygen, nutrients and humidity. To evaluate the role of humidity, the growth of bacteria and phage production within a culture device in a non-humidified environment and within the device in a humidity-controlled environment, i.e. 100% humidity, wherein the device was enclosed in a dish filled with wet napkins were compared. The results shown in FIGS. 10 and 11 indicate that maximizing humidity has no effect on bacterial growth in the culture or phage production. Therefore, maintaining the device even in a low humidity environment provides adequate conditions for bacterial growth and phage infection and production.

Figure 10:
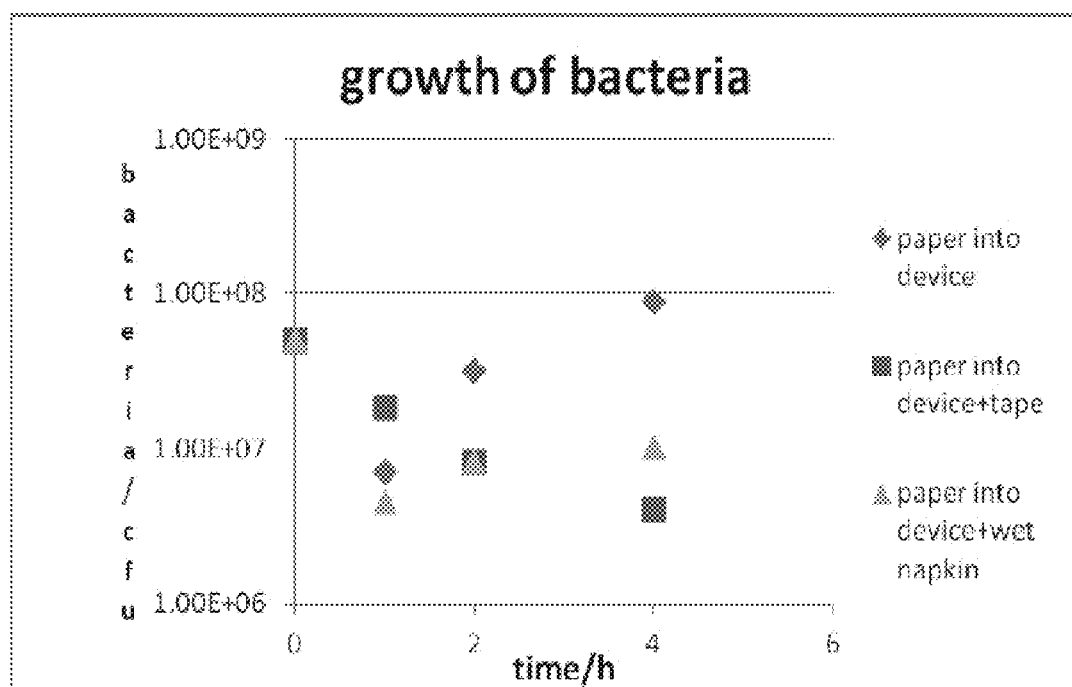
FIG. 10 depicts the results of an evaluation of the role of oxygen, nutrients and humidity on the growth of bacteria in the device.
Figure 11:
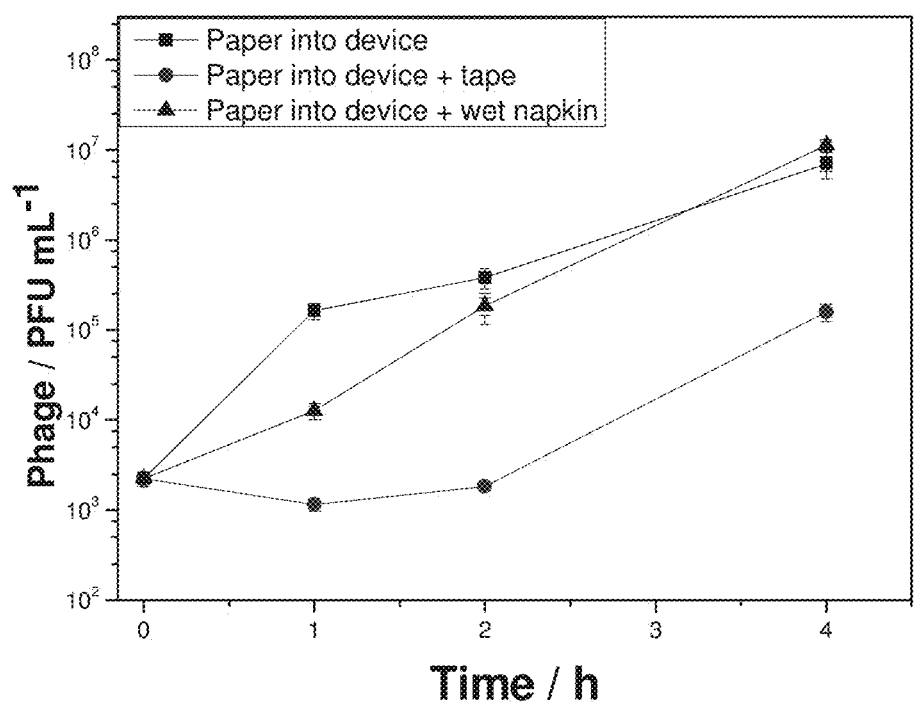
FIG. 11 depicts the results of an evaluation of the role of oxygen, nutrients and humidity on phage infection of bacteria in the device.

To estimate the role of oxygen flow through the PDMS membrane of the device, the flow of oxygen was ceased by covering the device with a gas-impermeable membrane, in this example an adhesive tape was used. The lack of oxygen induced rapid death of bacteria as shown in FIG. 10. The concentration of phage in this example of a hypoxic culture increased very slowly but was not entirely diminished (see FIG. 11).

The above studies were performed by using a culture device prepared as described above in the previous studies. Both sides were folded in order to start the infection and amplification reaction. In one device, the same amount of phage and *E. coli* as previously described were incubated with the PDMS membrane covered with adhesive tape to block flow of oxygen. In a second culture device, the same amount of phage and *E. coli* were incubated with a plaque with four pieces of wet porous hydrophilic material in order to control and maintain humidity inside the device during the assay. Each device was incubated to different times and then quantified by titration in 5 mL of LB media with the layer of paper and sponge from the device. Phages were growth using LB agar media with X-gal and incubated to 37° C.

These results demonstrate that the culture devices described herein allow a sufficient flow of oxygen through the gas-permeable membrane to provide adequate humidity control in the absence of traditional humidity controlling factors. Blocking the membrane suffocates the bacteria and inhibits growth.

Example 3

Preparation of Dormant Bacteriophage Construct

In one embodiment, preparation of the construct described in FIG. 12 is as follows.

Isolating Double Stranded Plasmid.

25 mL of 12-16 h culture of K-12 ER2738 *E. coli* from New England Biolabs (NEB) in LB medium was inoculated with 1 µL of M13KE phage ($10^{12}$ pfu/mL) (NEB), and shaken for 4-6 h at 37° C. Double stranded plasmid was isolated using QIAprep Spin Miniprep Kit™ (Qiagen), ethanol precipitated overnight and quantified by NanoDrop. Plasmid was checked by agarose gel electrophoresis (0.7% agarose, 100V, 40 min) for correct apparent size (4-6 Kb).

Incorporating (FLAG, TEV) Insert.

SacI and SpeI restriction enzyme recognition sites were incorporated into the plasmid using PCR with primers containing the sites (primers from IDT). The PCR reaction was assembled according to iProof High Fidelity DNA Polymerase Protocol from Bio-Rad™.

Cycling Conditions:

Initial denaturation at 98° C. for 30 s for one cycle, 20 cycles of denaturation at 98° C. for 10 s, annealing at 60.3° C. for 20 s and extension at 72° C. for 3 min and 30 s, then one final extension cycle at 72° C. for 5 min and hold at 4° C. Before digestion, PCR product was ethanol purified for 2 h to overnight and quantified by NanoDrop™. The Digestion reaction was assembled according to Fermentas Fast-Digest™ Restriction Enzyme Protocol for digestion of 1 µg DNA using Green buffer, and incubated for 15 min at 37° C. Digestion reaction was then loaded directly onto an agarose purification gel (0.7% agarose, 100V, 40 min). The band at 7-8 Kb was excised and DNA extracted using Fermentas GeneJet™ Gel Extraction Kit. DNA was eluted with 30 µL buffer EB and quantified using NanoDrop. The ligation reaction was assembled according to NEB T4 DNALigase™ Protocol for 100 ng digest, and incubated at 16° C. overnight before heat killing at 65° C. for 15 min.

Recombinant Phage.

5-10 ng of DNA from the ligation reaction was added to 25 µL of thawed competent cells (K-12 ER2738) and incubated on ice for 30 min before heating at 42° C. for 30 s. 250 µL of pre-heated SOB media was added to competent cells before shaking at 37° C. for 1 hour. Cells were then plated and incubated at 37° C. overnight. Single, isolated blue plaques were taken up and added to LB media and cultured overnight and shaken at 37° C. for 4 to 5 h. Cells were then spun down and phage-containing supernatant collected for treatment with PEG and NaI to extract single stranded phage DNA for sequencing.

N1N2-Protein A Fusion.

To create a fusion protein composed of both protein A, from *Staphylococcus aureus*, and N1N2 domains from pIII of Bacteriophage, PCR was used to amplify their corresponding DNA sequence's (M13KE vector and *S. aureus* cDNA). The PCR reaction of N1N2 was setup as follows; 10 µl of 5× iProof High Fidelity buffer (Bio-rad), 2.5 µl of 10 mM $MgCl_2$, 1 µl of 10 mM dNTP mix, 1 µl of 25 µM Primer 1 Forward (Integrated DNA Technologies), 1 µl of 25 µM Primer 2 Reverse (Integrated DNA Technologies), 3.75 µl Phage dsDNA (332 ng/µl), 2 µl DMSO, 28.25 µl DNase free water, and 0.5 µl iProof Polymerase (Bio-rad). The PCR program used was as follows; Initial Denaturation 98° C. for 30 s for 1 cycle, Denaturation 98° C. 10 s, Annealing 60° C. 20 s, and Extension 72° C. 20 s for 20 cycles, then a Final Extension 72° C. 5 min. The N1N2 PCR product was run on an agarose gel and gel extracted using a GeneJet™ Gel Extraction Kit (Fermentas). The concentration of N1N2 was determined by Nanodrop ND-1000 spectrophotometer (Thermo).

The PCR reaction of Protein A was setup as follows; 10 µl of 5× iProof High Fidelity buffer (Bio-rad), 5 µl of 10 mM $MgCl_2$, 1 µl of 10 mM dNTP mix, 1 µl of 25 µM Primer 2' Forward (Integrated DNA Technologies), 1 µl of 25 µM Primer 3 Reverse (Integrated DNA Technologies), 2 µl *Staphylococcus aureus* cDNA (632 ng/µl), 2 µl DMSO, 27.5 µl DNase free water, and 0.5 µl iProof Polymerase (Bio-rad). The PCR program utilized was Initial Denaturation 98° C. 30 s for 1 cycle, then 20 cycles of Denaturation 98° C. 10 s, Annealing 60° C. 20 s, and Extension 72° C. 30 s, the a Final extension 72° C. 5 min. The Protein A PCR product was run on an agarose gel and gel extracted using a GeneJet™ Gel Extraction Kit (Fermentas). The concentration of N1N2 was determined by Nanodrop.

To create the N1N2-Protein A fusion protein addition of the N1N2 and Protein A PCR products were added to the same PCR reaction. That reaction was setup as follows; 10 µl of 5× iProof High Fidelity buffer (Bio-rad), 5 µl of 10 mM $MgCl_2$, 1 µl of 10 mM dNTP mix, 1 µl of 25 µM Primer 1 Forward (Integrated DNA Technologies), 1 µl of 25 µM Primer 3 Reverse (Integrated DNA Technologies), 7.1 µl N1N2 PCR product (28.2 ng/µl), 16.9 µl Protein A PCR product (11.8 ng/µl), 2 µl DMSO, 5.5 µl DNase free water, and 0.5 µl iProof Polymerase (Bio-rad). The PCR program utilized was Initial Denaturation 98° C. 30 s for 1 cycle, then 20 cycles of Denaturation 98° C. 15 s, Annealing 61° C. 20 s, and Extension 72° C. 45 s, the a Final extension 72° C. 5 min. The N1N2-Protein A PCR product was run on an agarose gel and gel extracted using a GeneJet™ Gel Extraction Kit (Fermentas). The concentration of N1N2 was determined by Nanodrop.

Next pET-30(b) vector (Novagen) and N1N2-Protein A fusion PCR product were digested with Nco1 and Nde1 restriction enzymes. The two restriction enzyme digest's were setup as follows: 2 µl reaction buffer #3 (New England Biolabs), 1 µg pET-30(b)+vector or 1 ug N1N2-Protein A, 1 µl (10 U/µl) Nde1 (New England Biolabs) and 1 µl (10 U/µl) Nco1 (New England Biolabs), and add DNase free water up to 20 µl. This digestion mixture was incubated at 37° C. for 1.5 h. After digestion dephosphorylate sticky ends to prevent recircularization using TSAP enzyme and TSAP buffer (Invitrogen). The product was run on a gel to verify digestion and the gel extracted with Genejet™ gel extraction kit (Fermentas).

The 2 fragments (pET-30(b)+vector and N1N2-Protein A) were then ligated as follows: 1 µl T4 DNA Ligase (New England Biolabs), 1 µl 10× buffer (New England Biolabs), 2 µl restricted pET-30(b)+vector and 6 µl N1N2-Protein A fragment. This mixture was left at room temperature for 2 h.

The ligated vector was then cloned into DH5α competent cells (Invitrogen) plated on kanomyocin agar plates. The plates were incubated overnight at 37° C. and then scored for transformants the next day. Ten colonies were chosen for Colony PCR to confirm ligation and orientation of the insert. A primer flanking the 5' insertion site paired with our P3 Reverse primer was used. The PCR program utilized was Initial Denaturation 98° C. 30 s for 1 cycle, then 20 cycles of Denaturation 98° C. 15 s, Annealing 61° C. 20 s, and Extension 72° C. 45 s, then a Final extension 72° C. 5 min.

In addition to Colony PCR, we performed fluorescent sequencing reactions on the positive clones. The Big Dye™ sequencing system (Applied Biosystems) was utilized. The positive clones were collected and their plasmid was isolated by Miniprep™ (Qiagen) in order to transform them into an expression host to purify the recombinant protein. Isolated plasmid was cloned into BL21DE3 competent cells and plated on kanomyocin agar plates. Positive colonies were then grown in LB media (Fisher Scientific)+kanomyocin. The cells were then induced by IPTG (Invitrogen) and monitored until they had on OD600 of 0.6. Protein purification using a Protein A tag procedure was performed following a standard protocol familiar to a person skilled in the art.

Example 4

Protocols for Chemical Post-translational Modification

Protocol 1: Non-peptidic antigen, such as carbohydrate lipoarabinomannan (LAM) from *M. tuberculosis* can be easily introduced onto the phage by chemical modification of the N-terminal Cys residue resulting from TEV protease cleavage as shown in FIG. 14. Such phage would be sensitive to the presence of anti-LAM antibody, which is diagnostic of TB infection. Other modifications can include chemical oxidation of N-terminal Ser and ligation of hydrazine or hydroxylamine-containing LAM (or other molecules) to the resulting N-terminal aldehyde. Other chemical modification of internal or N-terminal cysteines, can be used, as described in the literature (maleimide coupling, native chemical ligation, etc). These examples demonstrate a system useful for detection of antibodies specific for the antigen displayed on the surface of the phage. However, this system can be modified for use in detect other molecules in a biological sample. Other components that can be fused to phage and NT include, but are not limited to, a protein having two distinct binding sites or a polynucleotide (which can facilitate binding of the N-terminal regions of the truncated coat protein via hybridization of complementary strands of polynucleotides).

Figure 15:
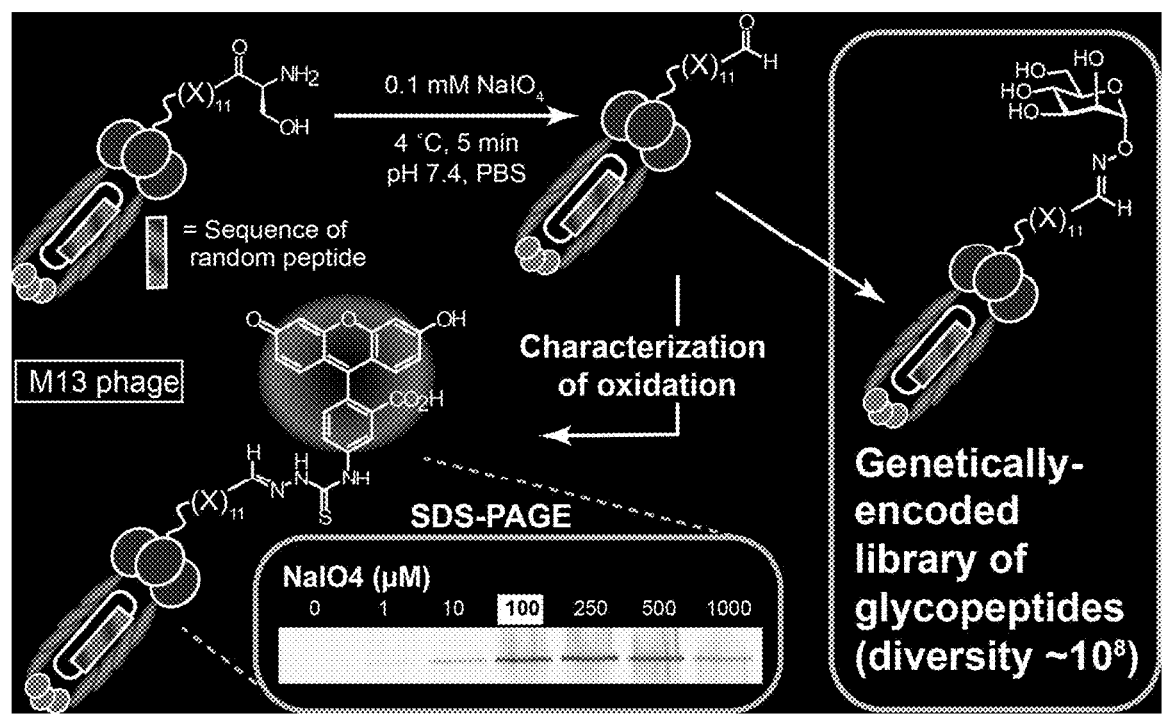
FIG. 15 depicts another strategy for conjugation of carbohydrate or any other recognition epitopes to specific location in phage protein.
Figure 16A:
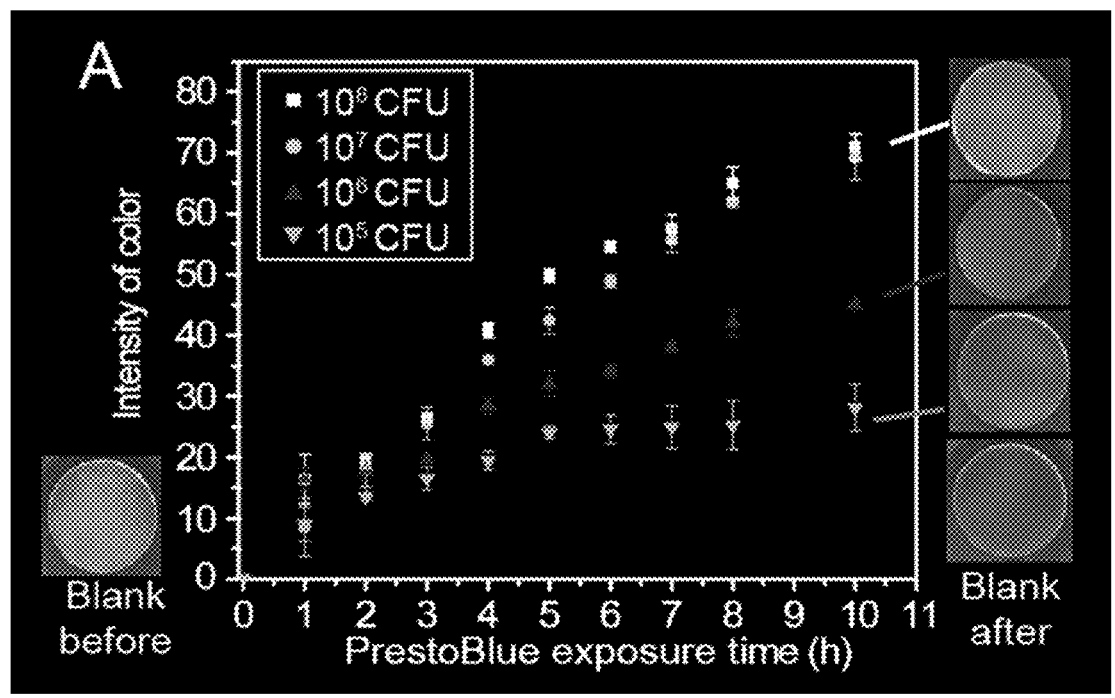
FIGS. 16A-E provide exemplary visualizations of bacterial growth using the culture device of the present application.
Figure 16B:
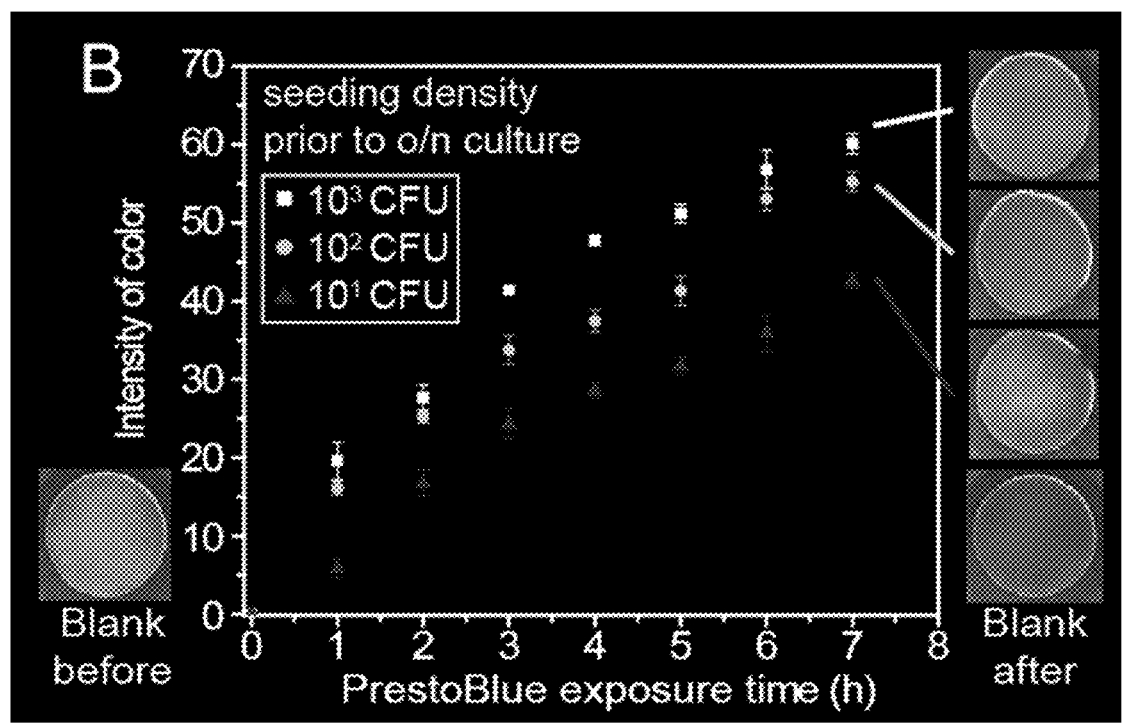
Figure 16C:
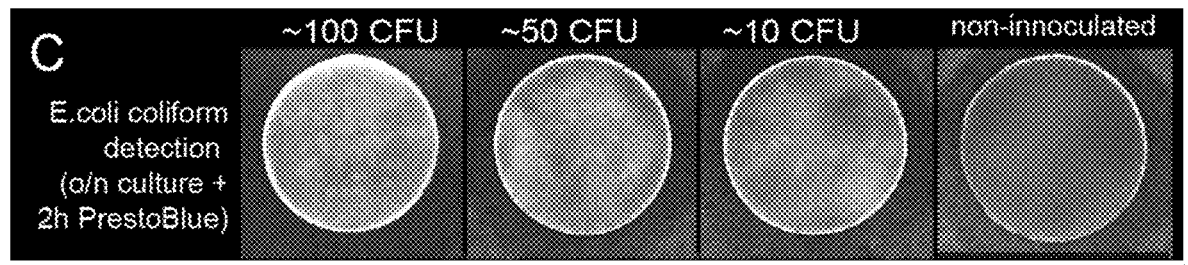
Figure 16D:
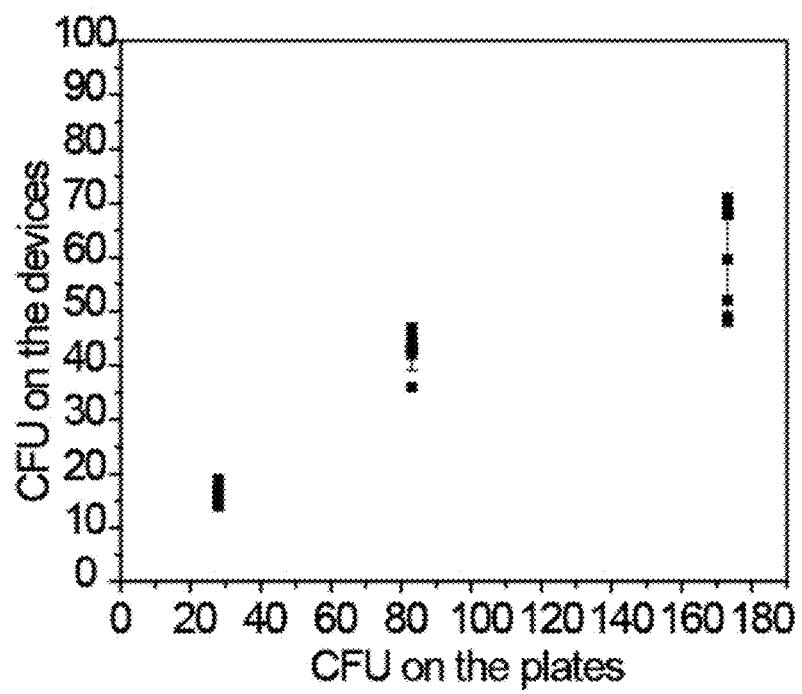
Figure 16E:
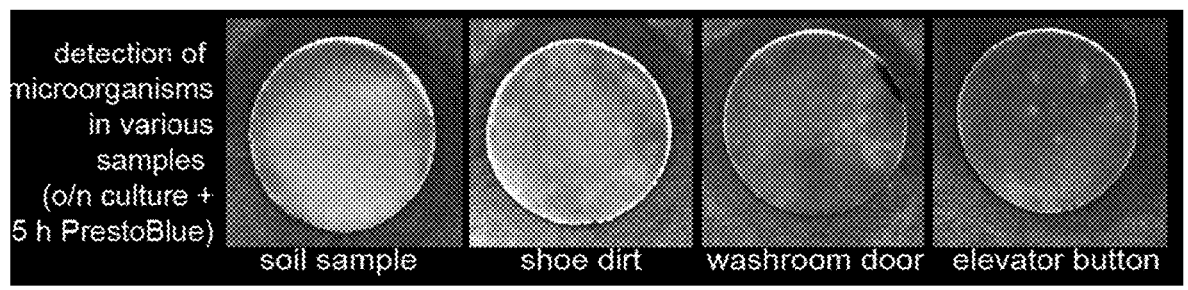

Protocol 2: Another strategy for conjugation of carbohydrate, or any other recognition epitope(s), to specific location in phage protein is depicted in FIG. 15. $(X)_{11}$ here denotes that preceding amino acids can be any amino acids (random peptide). Linking to a library of random peptides can be used for optimization of the linker length in the construct described in FIG. 13. The peptides can incorporate all or a part of the protease cleavage site, for example, cleavage with TEV protease leaves N-terminal serine. Mannose is shown as one example for simplicity. Other carbohydrates may be attached in a similar manner.

In one example, filamentous M13 phage carrying a LacZ reporter gene and displaying H$_2$N-SVEKNDQKTYHA peptide on pIII protein was used in a model assay system. Modification of peptides containing N-terminal serine using periodate oxidation followed by oxime ligation can be used when a serine is located in another region of the phage protein, for example, at the N-terminus of the truncated protein described in FIG. 12.

All reagents used in this protocol were first dissolved in DMF as a concentrated stock solution before adding into the solution of phage. To a 99 µL of phage solution from the stock (ca. $10^{12}$ pfu/mL in PBS, pH 7.4) was added 1 µL of sodium periodate (Sigma) to a concentration of 0.1 mM. The resulting solution was vortexed briefly, protected from exposure to light, and then reacted for 5 min on ice. The reaction was quenched by reacting with 1 mM of N-acetyl methionine (Sigma) for 10 min at room temperature.

The reaction efficiency was characterized using conjugation of fluorescent reagent (FIG. 15) or biotin instead of carbohydrate. Similar efficiency is expected for carbohydrate coupling. Labelling reagent, N-(aminooxyacetyl)-N'-(D-biotinyl) hydrazine (Invitrogen), was then added to a final concentration of 1 mM. Following incubation at room temperature for 18 h, the reaction mixture was precipitated with 50% volume of 15% (w/v) PEG/2.5 M NaCl for 2 h on ice to remove the excess reagents. The phage pellet was collected and re-dissolved in PBS buffer (pH 7.4). In order to characterize and quantify the efficiency of the conjugation, standard phage titering was performed to count how many biotinylated phage particles were captured by the streptavidin-coated magnetic bead (Bioclone, Inc.). A mixture of wild-type and biotinylated phage ($10^7$ phage particles each) was prepared and diluted with incubation buffer (0.1% (w/v) bovine serum albumin in PBS buffer, pH 7.4) to a final volume of 100 µL (here, wild type phage, which forms blue plaques on X-gal plates is used as an internal quantification control, which accounts for non-specific adsorption to the bead). 10 µL of phage solution was taken out for phage titering to determine the input of chemically-modified and wild type phage particles (by counting blue and white plaques). Before incubating 5 µL of the magnetic bead with the premixed phage solution, the bead storage solution was removed and the bead was washed with 1 mL of incubation buffer. The microcentrifuge tube containing the washed bead was centrifuged briefly to remove the remaining droplet. The bead was then incubated with 90 µL of the premixed phage solution for 15 min under room temperature with shaking at 2000 rpm. Following the incubation, the magnetic bead was captured by magnet separator (New England Biolabs) and the supernatant was used for phage titering to determine how many phage particles were not captured by the affinity bead.

Example 5

Test for Resistance to Antimicrobial Agents in Portable Culture Device

As described above, the presently described portable culture devices can be used to visualize bacterial growth any type of bacteria or other microorganism. The present Example demonstrates that the presence of bacterial growth could be visualized using Alamar Blue dye (see, FIGS. 16 A-E and 17). Both laboratory strains and environmental strains of bacteria were visualized by this method.

Figure 19A:
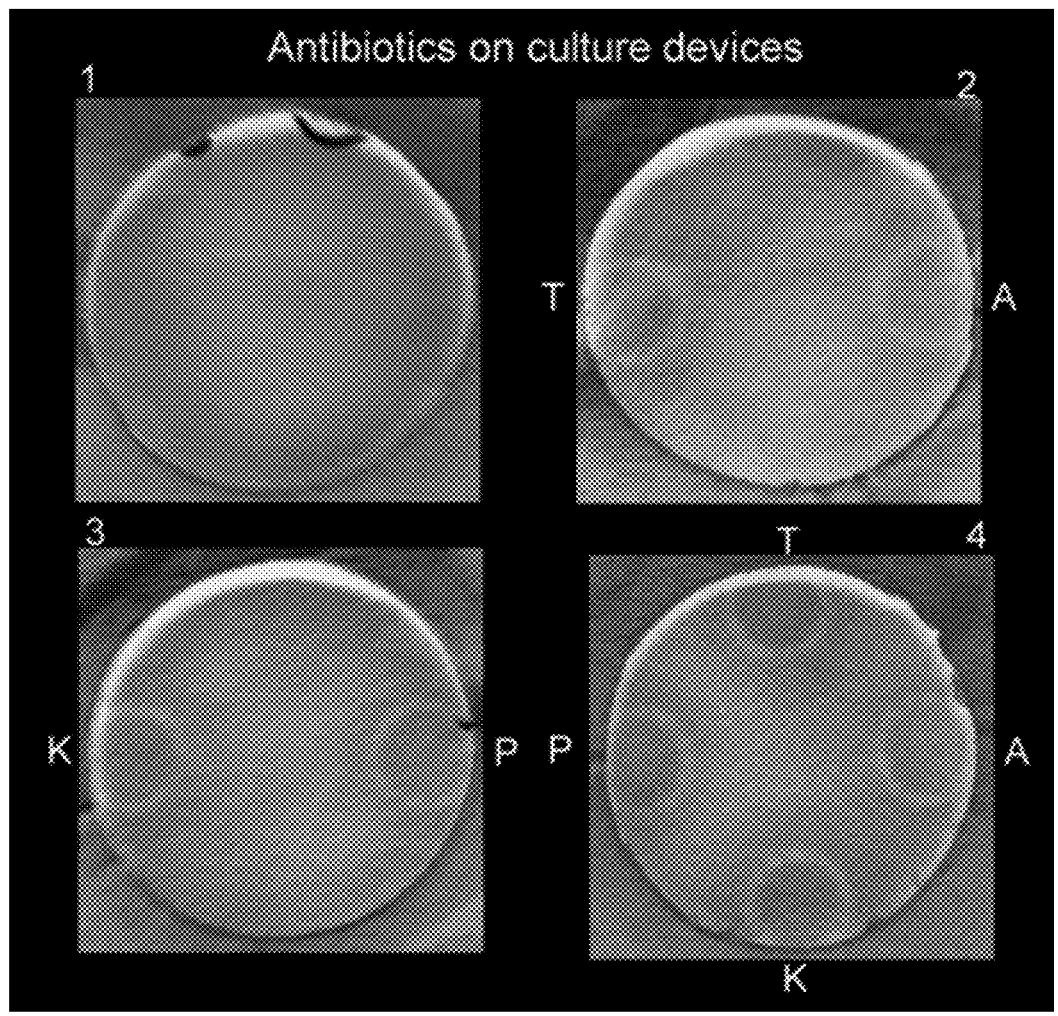
FIGS. 19A and 19B show the antibiotic resistance of mCherry $E.\ coli$ $10^6$ CFU to ampicillin (A), tetracycline (T), penicillin-streptomycin (P) and kanamycin (K) in culture device. Each device was inoculated with $10^6$ CFU of $E.\ coli$, cultured for 18 hours at 37° C., sprayed with Alamar blue and visualized 4 hours later.
Figure 19B:
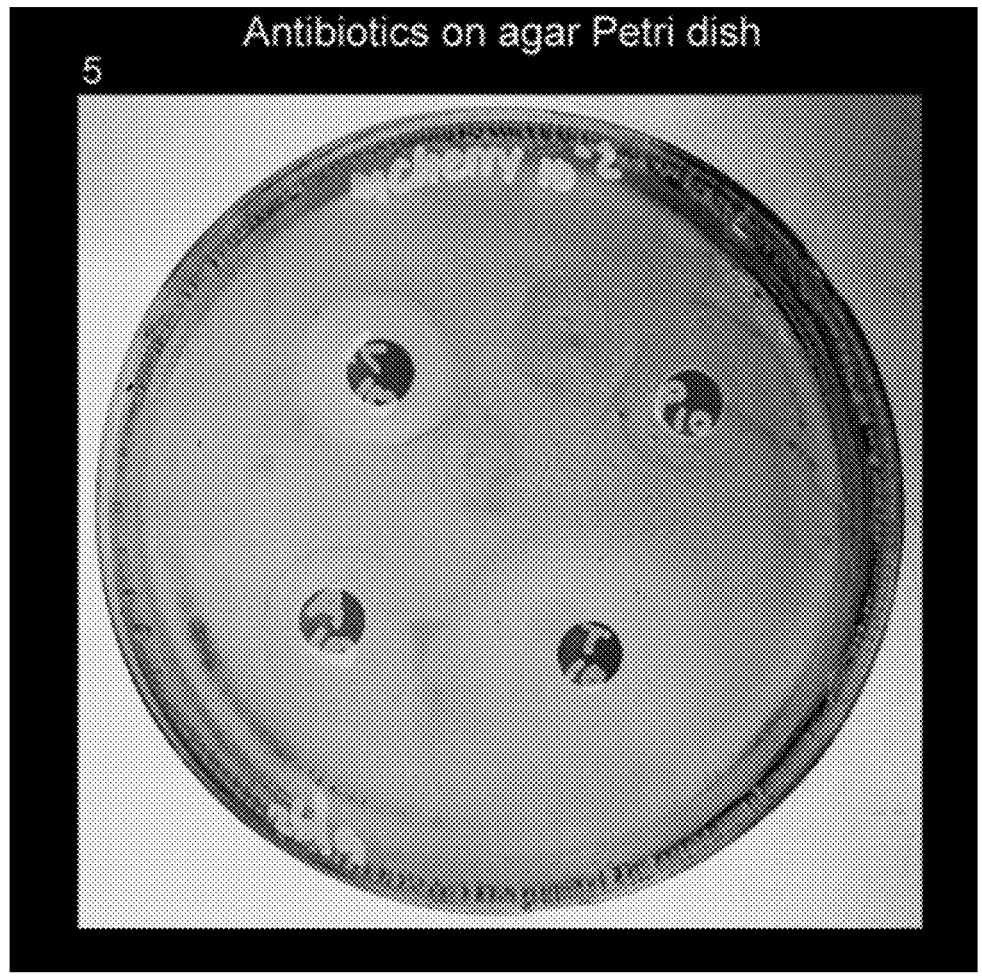
Figure 20A:
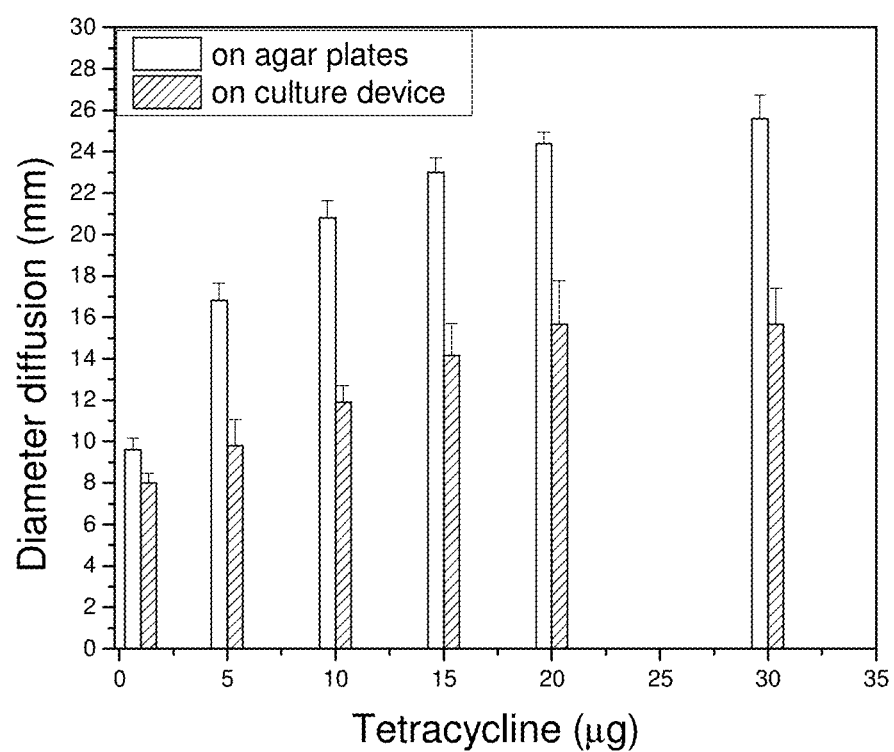
FIG. 20A graphically shows the susceptibility of mCherry $E.\ coli$ $10^6$ CFU to Tetracycline (1-30 µg) in culture device. Comparison of diameter of diffusion between agar plates and culture devices.
Figure 20B:
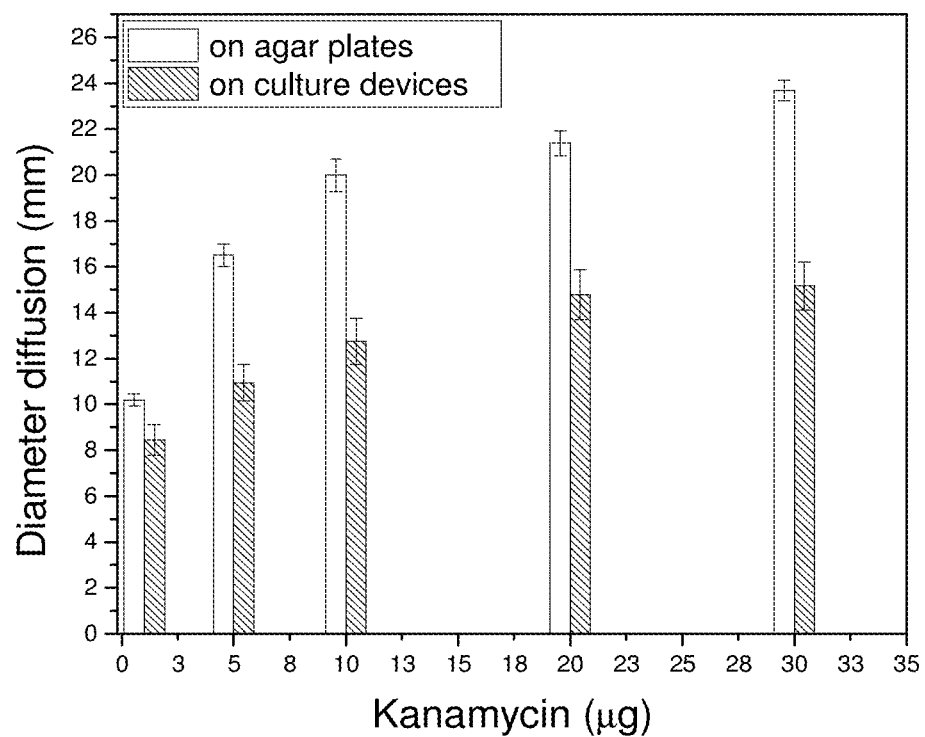
FIG. 20B graphically shows the susceptibility of mCherry $E.\ coli$ ($10^6$ CFU) to Kanamycin (1-30 µg) in culture device. Comparison of diameter of diffusion to Kanamycin antibiotic between agar plates and culture devices.
Figure 21A:
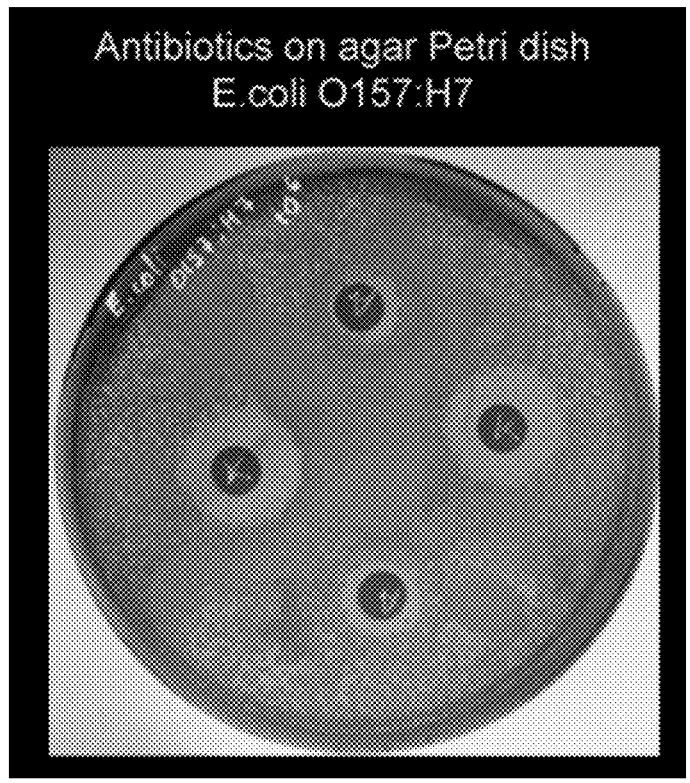
FIGS. 21A and 21B show the susceptibility of $E.\ coli$ O157:H7 $10^6$ CFU to ampicillin and kanamycin antibiotics in agar Petri dish and culture device.
Figure 21B:
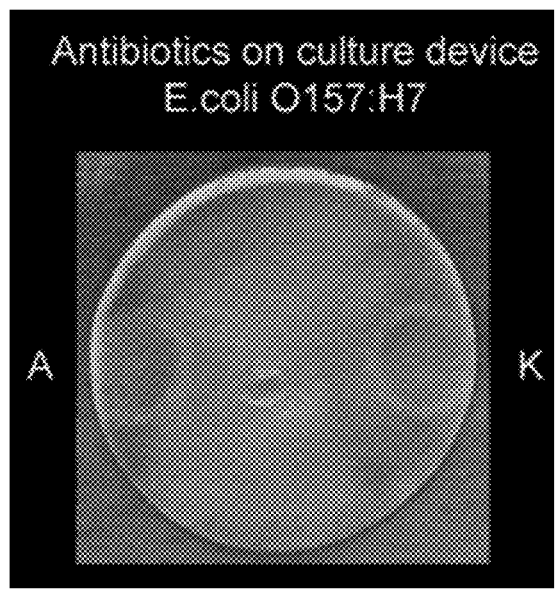
Figure 22A:
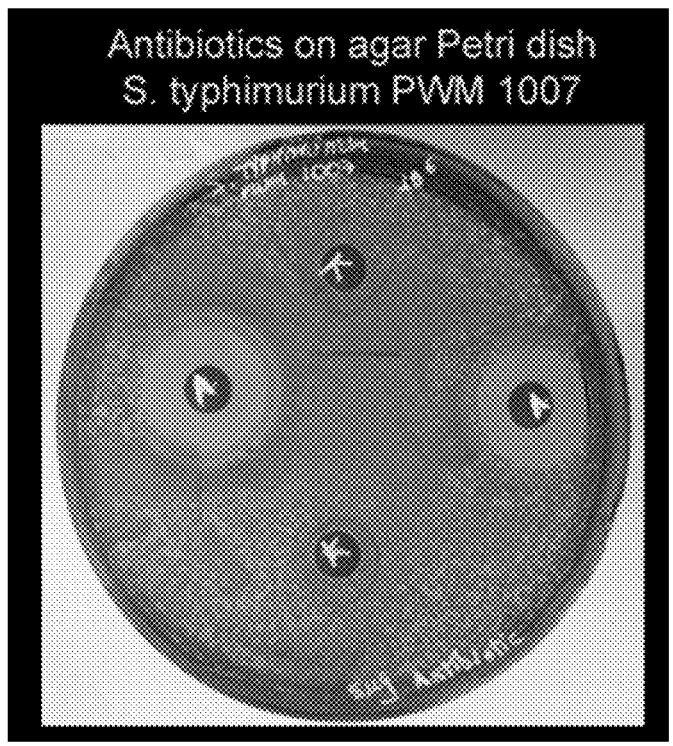
FIGS. 22A and 22B show the susceptibility and resistance of $Salmonella\ typhimurium$ PWM 1007 to ampicillin and kanamycin antibiotics in agar Petri dish and culture device.
Figure 22B:
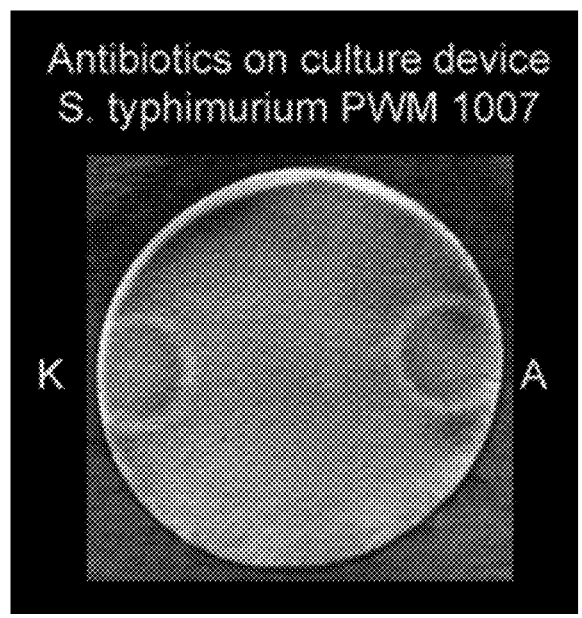

Also demonstrated in the present example, is the use of the present portable culture device to evaluate antibiotic resistance in microorganisms. To this end, the culture area of the device was patterned with specific antibiotics. Diffusion of the antibiotics in the devices lead to formation of growth and no-growth zones (see FIGS. 18 and 19); the sizes of which were similar to those formed in a parallel antibiogram test in Petri Dishes (see FIGS. 20 and 21).

Devices with culture areas of 3 cm in diameter were useful in testing for antibiotic resistance to up to four antibiotics simultaneously (see FIG. 19).

Experimental Details

PrestoBlue™ (Invitrogen) is a fluorescent dye that is used to quantify and evaluate the viability of cells. The reagent contains a blue dye (resazurin) that is reduced to the highly fluorescent red (resorufin) in the presence of diaphorase enzyme.

Figure 17:
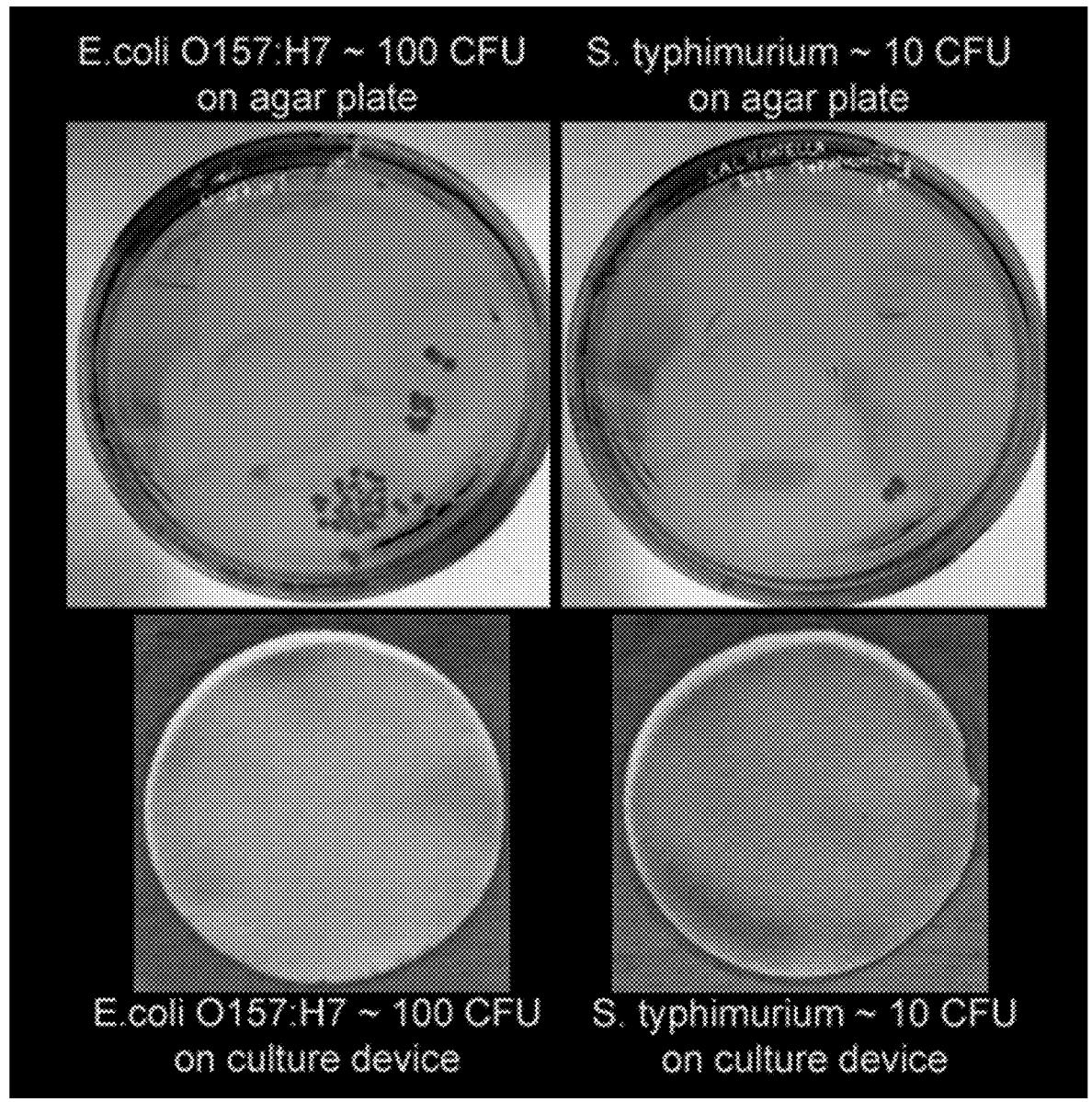
FIG. 17 provides images of culture plates showing the detection of microorganisms on agar plates and the culture device of the present application.

PrestoBlue™ assays were performed in portable culture devices by spraying the culture regions of the devices with a solution of resazurin dye (see, FIG. 17). Viable colonies of bacteria were detected as red spots after incubation for brief period of time (10 minutes to 4 hours) (see, FIG. 16 A-E, note that the red spots show as dark spots in the black and white pictures).

Figure 18:
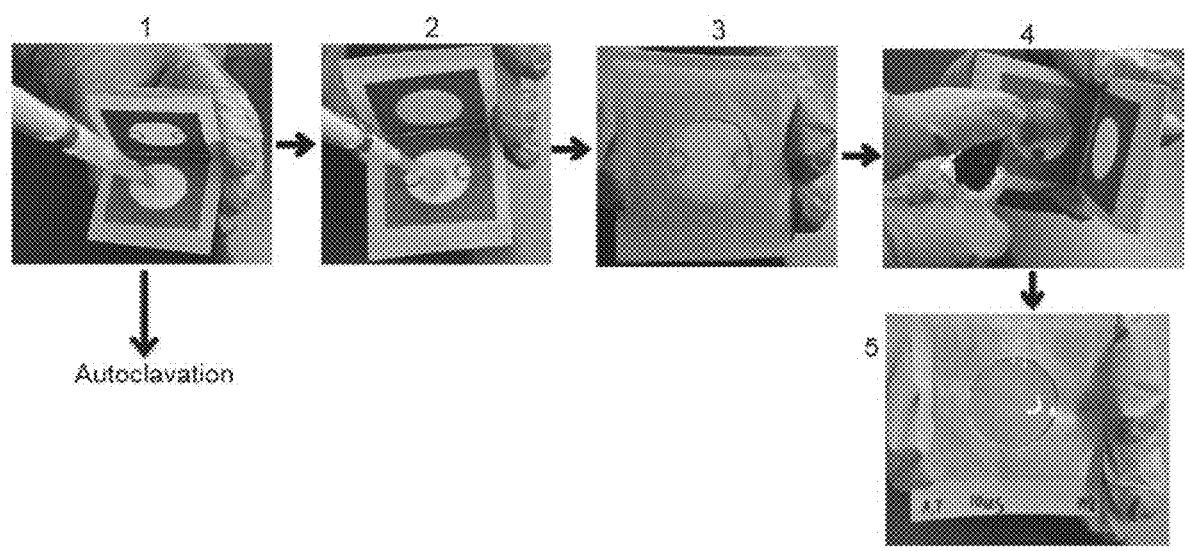
FIG. 18 is a portable culture device methodology for antibiotic resistance in $E.\ coli$.

The steps used in this study to detect antibiotic resistance are shown in the photographs of FIG. 18.

An antibiogram is the result of standard laboratory testing for the sensitivity of an isolated bacterial strain to different antibiotics. To compare a standard antibiogram test in Petri Dishes to a test to detect antibiotic resistance using the present portable culture devices, both agar plates and culture devices were inoculated the same amount of bacteria (for example, $10^6$ colony forming units (CFU)). In the culture devices, the paper area used for culture contained a 7 mm zone patterned with antibiotic. For the standard test a 7 mm disk soaked with antibiotic was placed in the agar dish. The results of the antibiotic resistance assays in the culture devices were revealed after overnight incubation and spraying PrestoBlue™ on the culture zone. Growth/no-growth areas were revealed as blue (no growth) and red (growth) color in the devices after 2 to 4 hours.

The microorganisms tested were K12 *E. coli* with resistance to ampicillin and penicillin, *E. coli* O157:H7 with resistance to ampicillin, and *Salmonella typhimurium* PWM 1007 with resistance to kanamycin. The antibiotics tested in culture devices were tetracycline, kanamycin, ampicillin and penicillin-streptomycin. The size of diffusion observed after incubation was similar in plates and culture devices (see, FIGS. 19A, 19B, 20A, 20B, 21A, 21B, 22A and 22B), indicating that the present portable culture devices can be used successfully in the detection of antibiotic resistance in microorganisms.

Example 6

Using Portable Culture Device with Phage-based Detection of Soluble Biomarkers

In this example a mixture of *E. coli* bacteria and engineered phage was used to demonstrate that AATA (avalanche analyte-triggered amplification) can be used to successfully detect analyte for which the phage is engineered.

Figure 23A:
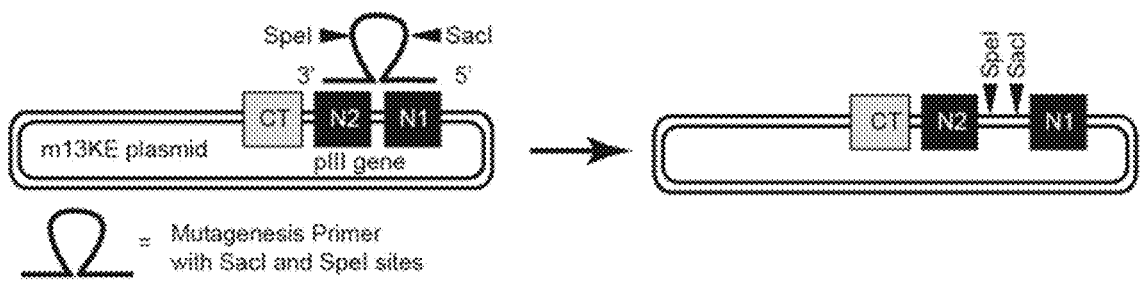
FIGS. 23A to 23E show cloning steps that generate AATA-vector.
Figure 23B:
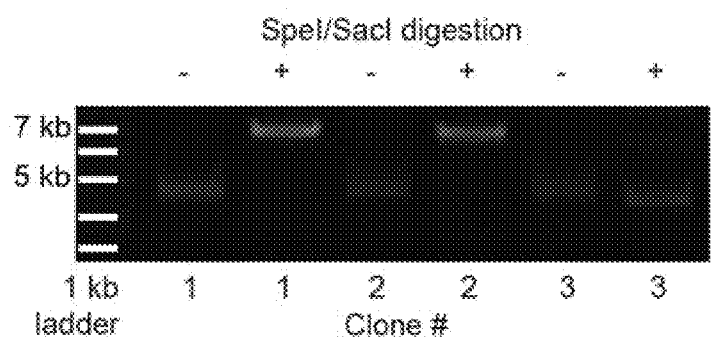
Figure 23C:
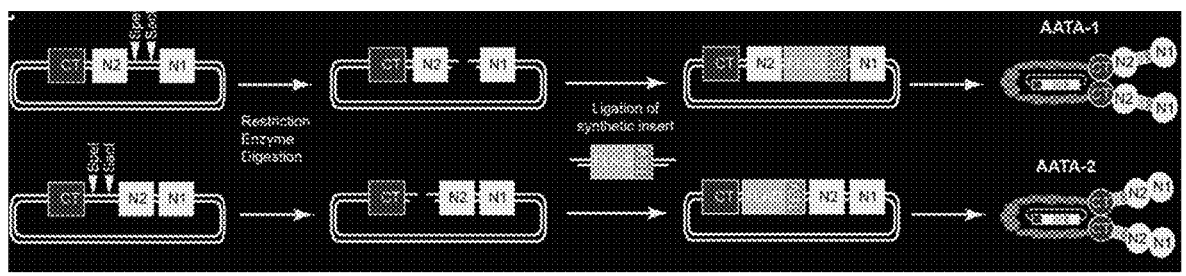
Figure 23D:
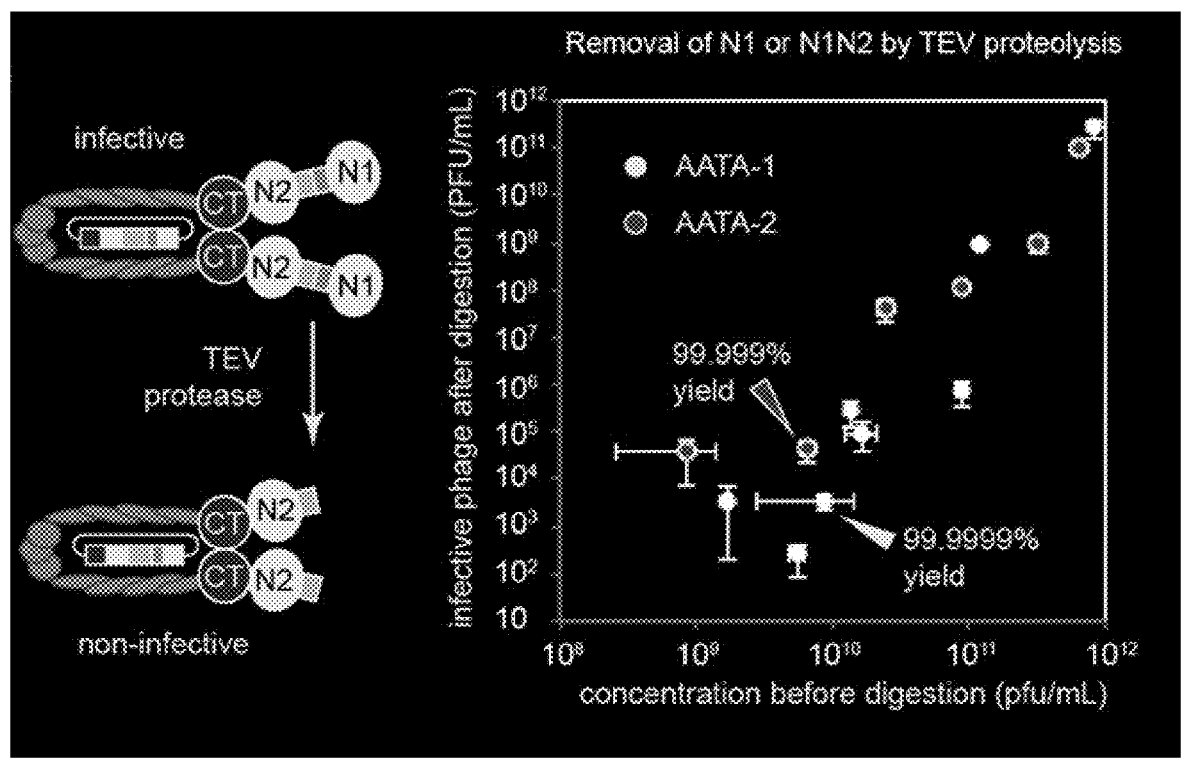
Figure 23E:
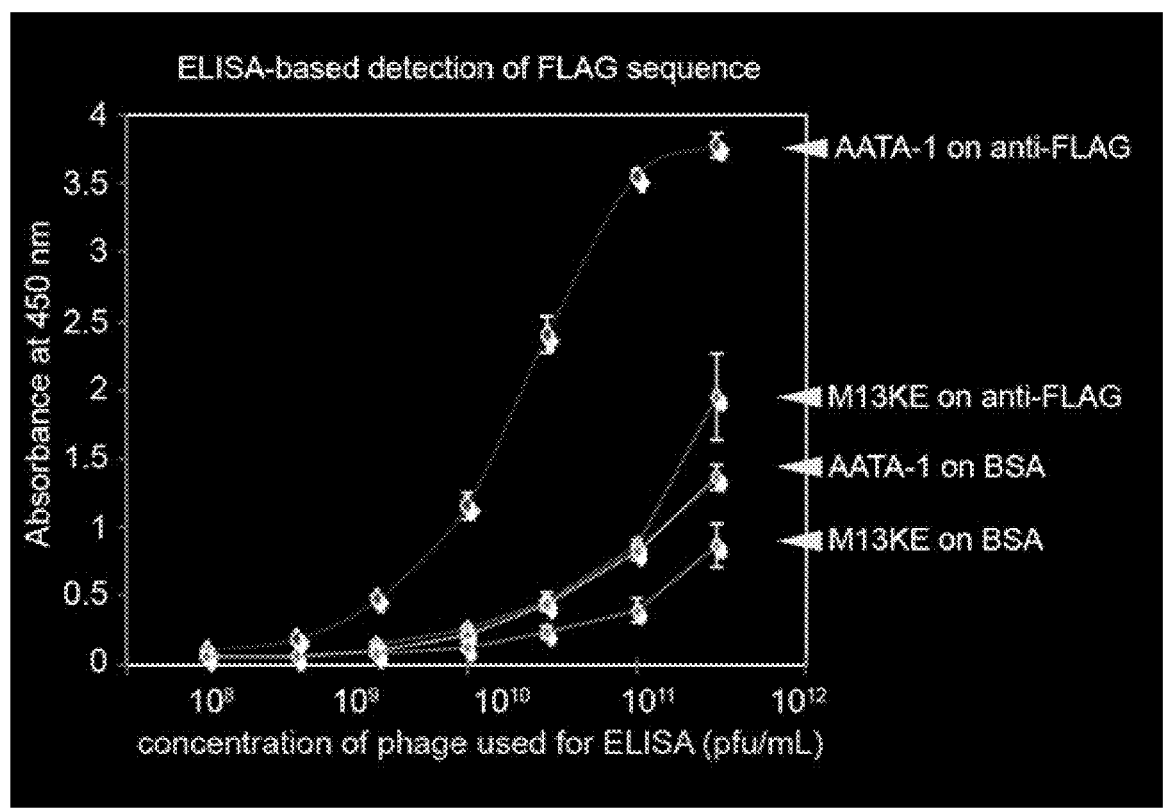

In this example, the phage was engineered to detect soluble antibodies. The steps for engineering the phage are shown in FIGS. 23A and C. The process was a combination of genetic engineering to introduce cleavable linkers and recognition epitopes for antibody (here, FLAG peptide). Second step is digestion of the phage with protease to remove the infection receptor and render phage non infective.

Figure 24A:
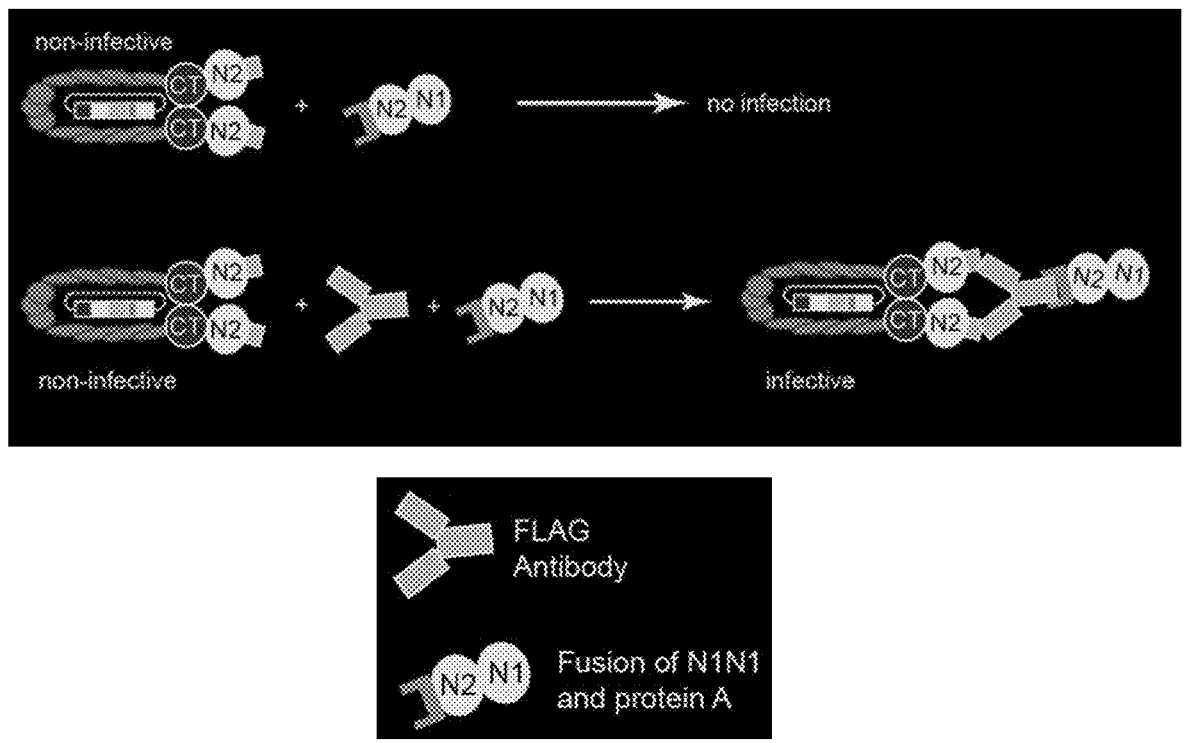
FIGS. 24A and 24B show a schematic (FIG. 24A) and graph (FIG. 24B) of the reconstitution of infectivity of AATA phage.
Figure 24B:
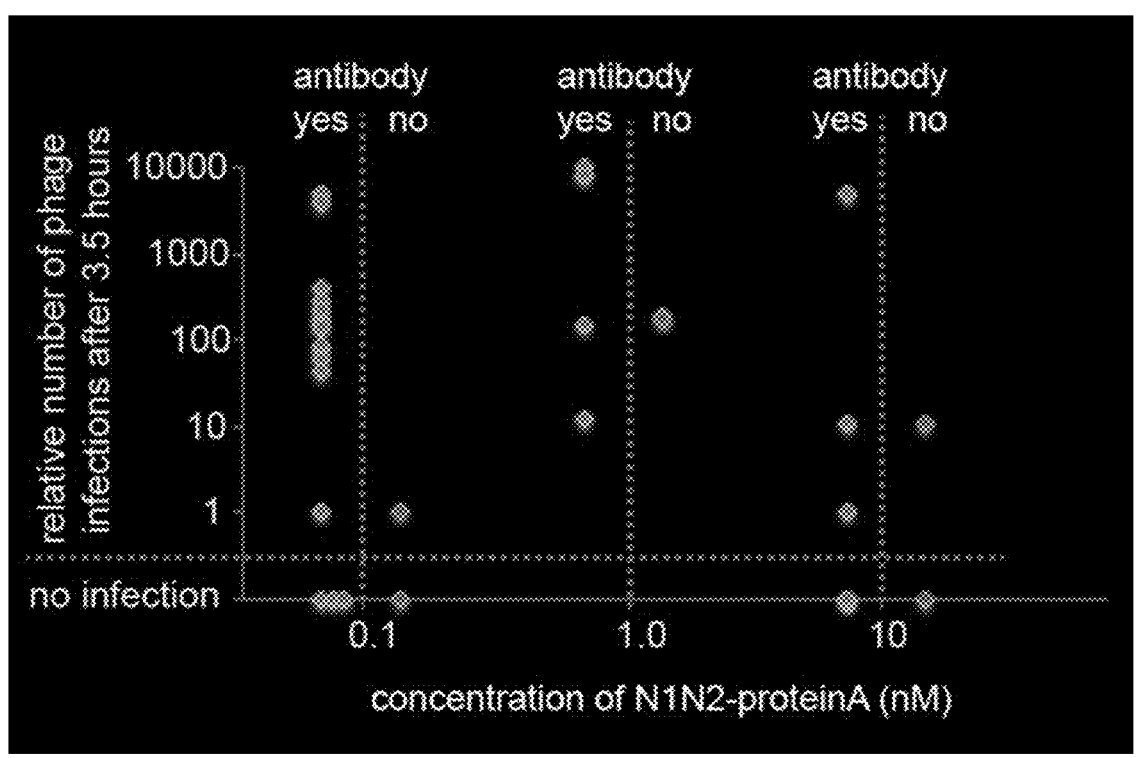

The phage designed as described in FIGS. 23A and B is non-infective and displays an antigen that can recruit a specific antibody. Binding of the antibody recruits the infection receptor (N1N2-proteinA) and renders phage infective (FIGS. 24A and B).

The phage was mixed with a solution of antibody (20 nM final concentration or none) and a solution of N1N2-proteinA fusion (at various concentrations). In the presence of FLAG antibody, re-emergence of infective phage particles was detected. Significantly fewer particles were observed in the absence of antibody. Concentration of N1N2-proteinA was an important parameter regulating infectivity. Few infection events were observed when concentration of N1N2-ProteinA was below 0.1 nM (not shown). Infection was detected by formation of plaques in agar, which, in this example, indicated the presence of specific antibody in solution. Infection was not restored when no antibody was added.

Similar detection of the infection can be performed in the presently described culture device using AATA to allow point-of-care detection of specific antibodies.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

---

The invention claimed is:

1. A method for detecting a substance of interest in a sample, comprising the steps of:
   a) introducing the sample to a mixture of dormant bacteriophage, bacteria and a soluble N-terminal fragment of a phage coat protein, wherein the dormant bacteriophage comprises a reporter gene, and a coat protein from which an N-terminal portion has been removed to produce a truncated coat protein that renders the bacteriophage non-infective and wherein the truncated coat protein displays a first binding molecule on the surface of the dormant bacteriophage that specifically binds to the substance of interest;
   b) incubating the mixture of the dormant bacteriophage and bacteria in the presence of the sample and a second binding molecule that specifically binds to the substance of interest, wherein said second binding molecule is fused to the N-terminal portion of coat protein such that binding complex formation between the dormant bacteriophage, the substance of interest and the second binding molecule activates the dormant bacteriophage to become infective;
   c) culturing the activated bacteriophage with the bacteria; and
   d) monitoring for expression of the reporter gene as an indicator of the presence of the substance of interest in the sample.

2. The method according to claim 1, wherein the bacteriophage is a filamentous bacteriophage.

3. The method according to claim 2, wherein the filamentous bacteriophage is fd, M13, f1, If1, Ike, Zj/2, Ff, Xf, Pf1 or Pf3.

4. The method of claim 1, wherein the first binding molecule is a peptide, a glycopeptide or a non-peptide molecule.

5. The method of claim 1, wherein the substance of interest is an antibody, an antigen or an analyte.

6. A method for detecting a substance of interest in a sample, comprising the steps of:
   a) introducing the sample to a mixture of dormant bacteriophage, bacteria and a soluble N-terminal fragment of a phage coat protein, wherein the dormant bacteriophage comprises a reporter gene, and a coat protein from which an N-terminal portion has been removed to produce a truncated coat protein that renders the bacteriophage non-infective and wherein the truncated coat protein displays a first binding molecule on the surface of the dormant bacteriophage that specifically binds to the substance of interest;
   b) incubating the mixture of the dormant bacteriophage and bacteria in the presence of the sample and a second binding molecule that specifically binds to the substance of interest, wherein said second binding molecule is fused to the N-terminal portion of coat protein such that binding complex formation between the dormant bacteriophage, the substance of interest and the second binding molecule activates the dormant bacteriophage to become infective;
   c) culturing the activated bacteriophage with the bacteria; and
   d) monitoring for expression of the reporter gene as an indicator of the presence of the substance of interest in the sample,
   which method is performed employing a portable culture device, which device comprises a continuous fluid impermeable material having first and second culture strips therein:
   wherein
      i) the first culture strip has an inner surface and comprises at least one culture region within a first strip of fluid impermeable material, the first culture strip having an adhesive on its inner surface; and
      ii) the second culture strip has an inner surface comprising at least one culture region within a second strip of fluid impermeable material, the second culture strip having an adhesive on its inner surface, wherein each of the at least one culture region of the second culture strip corresponds to one of the at least one culture region of the first culture strip to form a culture region pair,
   wherein each culture region comprises an inner layer of porous hydrophilic material and at least one culture region in each culture region pair comprises an outer layer of a gas permeable membrane, and
   wherein the device is moveable between an open condition and a closed condition in which the first and second culture strips are releasably adhered via the inner adhesive surfaces such that the culture regions in each culture pair are aligned and the outer gas permeable membrane or gas permeable membranes are exposed to the environment to permit gas flow to the interior of the device.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: FLAG peptide or epitope

<400> SEQUENCE: 1
```

```
Asp Tyr Lys Asp Asp Asp Lys
1               5
```

<210> SEQ ID NO 2
<211> LENGTH: 24
<212> TYPE: DNA
<213> ORGANISM: Artificial Sequence
<220> FEATURE:
<223> OTHER INFORMATION: Portion of the sequence of M13 phage

<400> SEQUENCE: 2
gagggtggtg gctctgaggg tggc                                    24

<210> SEQ ID NO 3
<211> LENGTH: 12
<212> TYPE: DNA
<213> ORGANISM: Artificial Sequence
<220> FEATURE:
<223> OTHER INFORMATION: forward primer

<400> SEQUENCE: 3
tgtggttgat ca                                                 12

<210> SEQ ID NO 4
<211> LENGTH: 12
<212> TYPE: DNA
<213> ORGANISM: Artificial Sequence
<220> FEATURE:
<223> OTHER INFORMATION: reverse primer

<400> SEQUENCE: 4
ctcgagttat tt                                                 12

<210> SEQ ID NO 5
<211> LENGTH: 51
<212> TYPE: DNA
<213> ORGANISM: Artificial Sequence
<220> FEATURE:
<223> OTHER INFORMATION: complete insert sequence

<400> SEQUENCE: 5
agctcgaaaa cctgtatttt cagtcggact acaaggacga cgatgacaag a       51

<210> SEQ ID NO 6
<211> LENGTH: 51
<212> TYPE: DNA
<213> ORGANISM: Artificial Sequence
<220> FEATURE:
<223> OTHER INFORMATION: complete insert sequence - reverse

<400> SEQUENCE: 6
ctagtcttgt catcgtcgtc cttgtagtcc gactgaaaat acaggttttc g       51

<210> SEQ ID NO 7
<211> LENGTH: 12
<212> TYPE: PRT
<213> ORGANISM: Artificial Sequence
<220> FEATURE:
<223> OTHER INFORMATION: filamentous M13 phage carrying a LacZ reporter
      gene on pIII protein

<400> SEQUENCE: 7

```
Ser Val Glu Lys Asn Asp Gln Lys Thr Tyr His Ala
1               5                   10
```